(12) United States Patent
Walters et al.

(10) Patent No.: US 10,682,128 B2
(45) Date of Patent: Jun. 16, 2020

(54) VASCULAR CLOSURE DEVICE WITH LOCKING ASSEMBLY FOR A TAMPER

(71) Applicant: Arrow International, Inc., Wayne, PA (US)

(72) Inventors: Greg A. Walters, Exton, PA (US); Joseph Todd Grintz, Glenmoore, PA (US)

(73) Assignee: Arrow International, Inc., Wayne, PA (US)

(*) Notice: Subject to any disclaimer, the term of this patent is extended or adjusted under 35 U.S.C. 154(b) by 0 days.

(21) Appl. No.: 16/324,333

(22) PCT Filed: Aug. 8, 2017

(86) PCT No.: PCT/US2017/045885
§ 371 (c)(1),
(2) Date: Feb. 8, 2019

(87) PCT Pub. No.: WO2018/031539
PCT Pub. Date: Feb. 15, 2018

(65) Prior Publication Data
US 2019/0343497 A1    Nov. 14, 2019

Related U.S. Application Data

(60) Provisional application No. 62/374,177, filed on Aug. 12, 2016.

(51) Int. Cl.
*A61B 17/00* (2006.01)
*A61B 17/04* (2006.01)

(52) U.S. Cl.
CPC .............. *A61B 17/0057* (2013.01); *A61B 2017/00623* (2013.01); *A61B 2017/00654* (2013.01);
(Continued)

(58) Field of Classification Search
CPC ...... A61B 17/0057; A61B 2017/00659; A61B 2017/0475; A61B 2017/00623; A61B 2017/00654
See application file for complete search history.

(56) References Cited

U.S. PATENT DOCUMENTS 8,652,166 B2 * 2/2014 Åkerfeldt .......... A61B 17/0057
606/213
2005/0085852 A1    4/2005 Ditter
(Continued)

FOREIGN PATENT DOCUMENTS

WO    2011166498 A1    12/2011

OTHER PUBLICATIONS

Martin Kamp, International Search Report and the Written Opinion, dated Nov. 8, 2017, 15 pp.

*Primary Examiner* — Katherine M Shi
*Assistant Examiner* — Michael G Mendoza
(74) *Attorney, Agent, or Firm* — Offit Kurman, P.C.; Gregory A. Grissett

(57) ABSTRACT

A vascular closure device includes a deployment assembly, a sealing unit carried by the deployment assembly, and a tamper carried by the deployment assembly and that is disposed along a suture with respect to the sealing unit. The vascular closure device includes a locking assembly coupled to the tamper so as to selectively inhibit advancement of the tamper along the suture in the distal direction toward the sealing unit. The locking assembly is adapted to transition from A) a locked configuration where the tamper is inhibited from sliding along the suture, into B) an unlocked configuration where the tamper is slidable along the suture in the distal direction and into contact with the sealing unit.

20 Claims, 17 Drawing Sheets

(52) U.S. Cl.
CPC ............ *A61B 2017/00659* (2013.01); *A61B 2017/0475* (2013.01)

(56) References Cited

U.S. PATENT DOCUMENTS

| | | | |
|---|---|---|---|
| 2005/0085855 A1 | 4/2005 | Forsberg | |
| 2006/0265006 A1* | 11/2006 | White | A61B 17/0057 606/232 |
| 2013/0178895 A1 | 7/2013 | Walters et al. | |
| 2014/0336672 A1* | 11/2014 | Walters | A61B 17/0057 606/139 |

\* cited by examiner

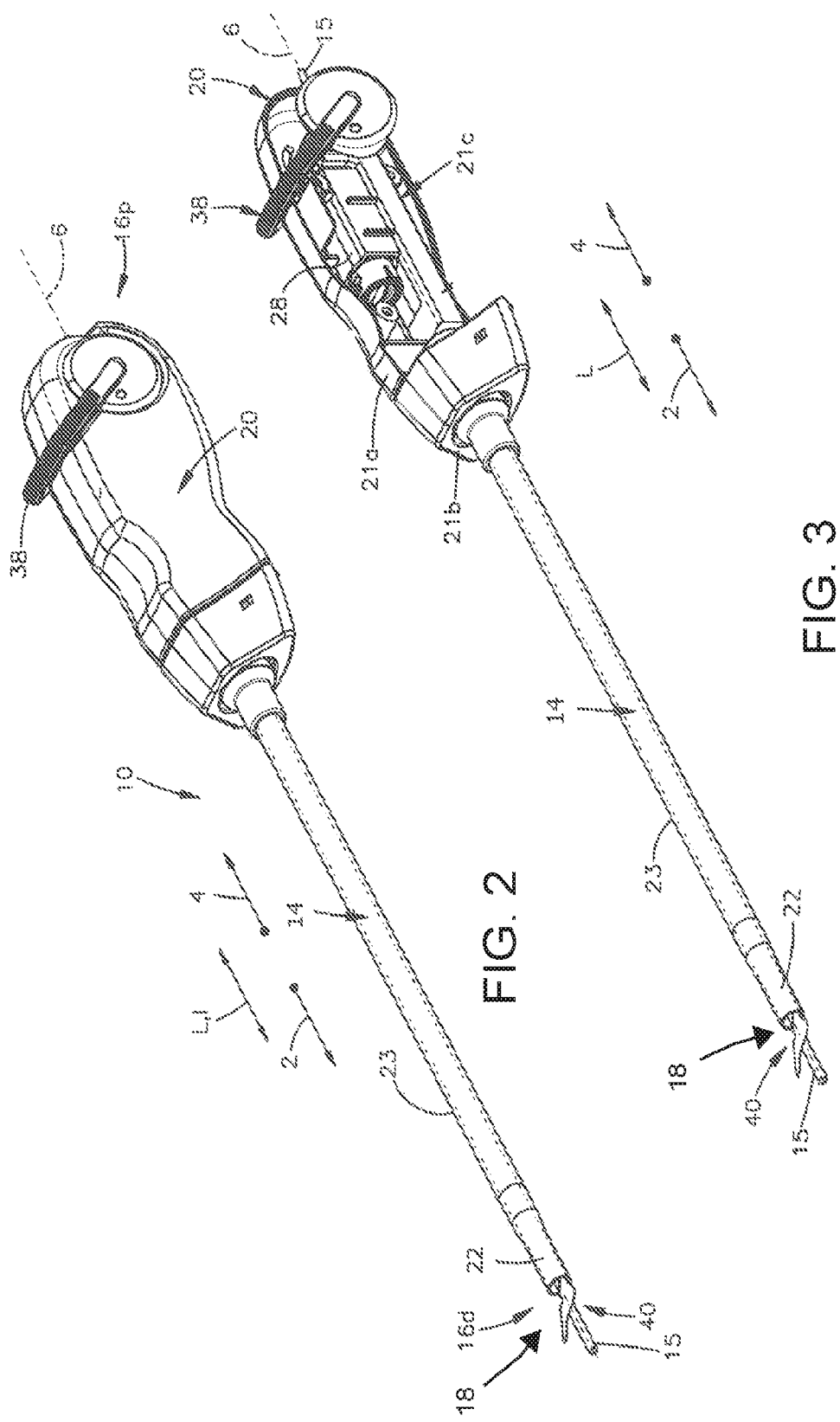

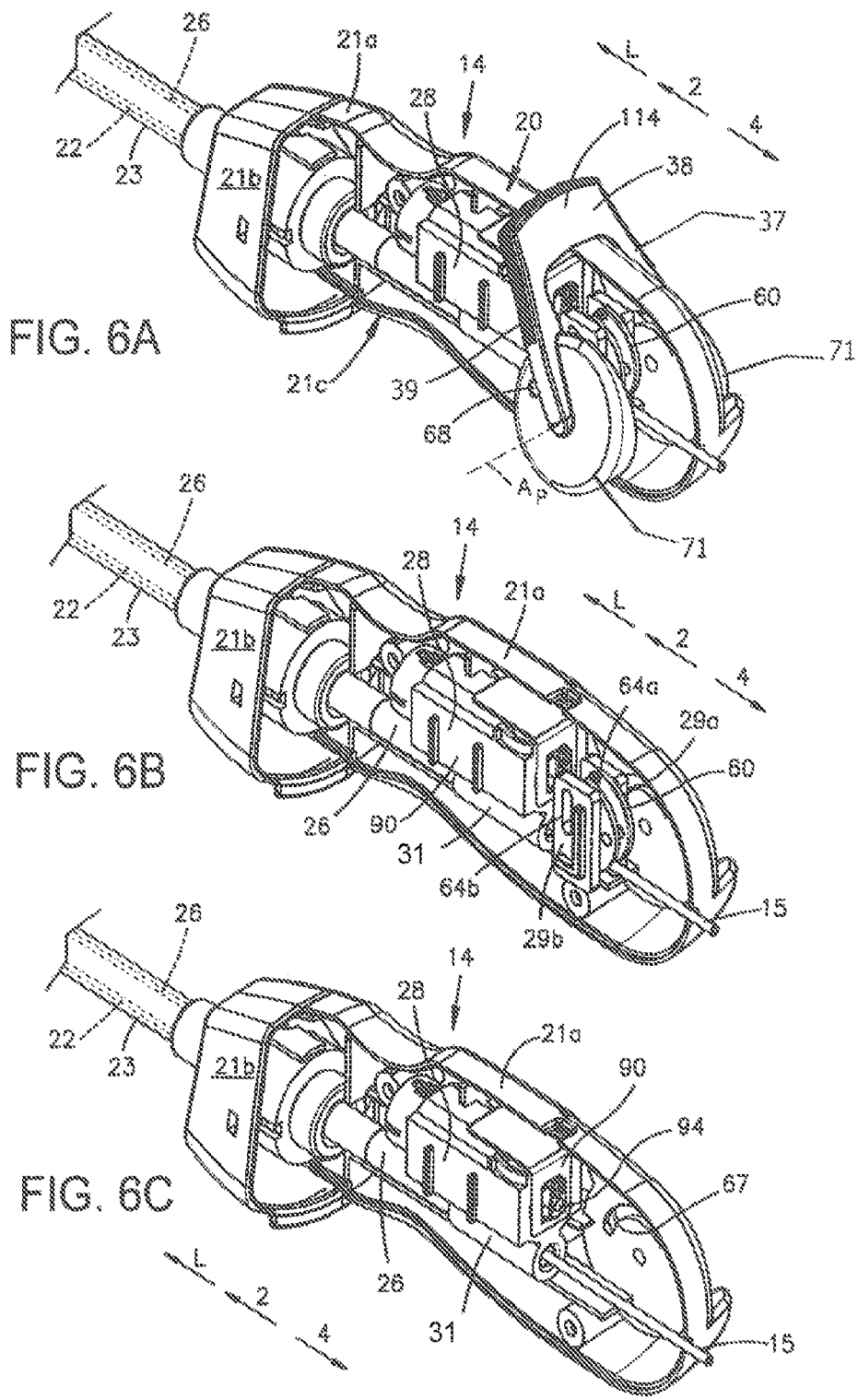

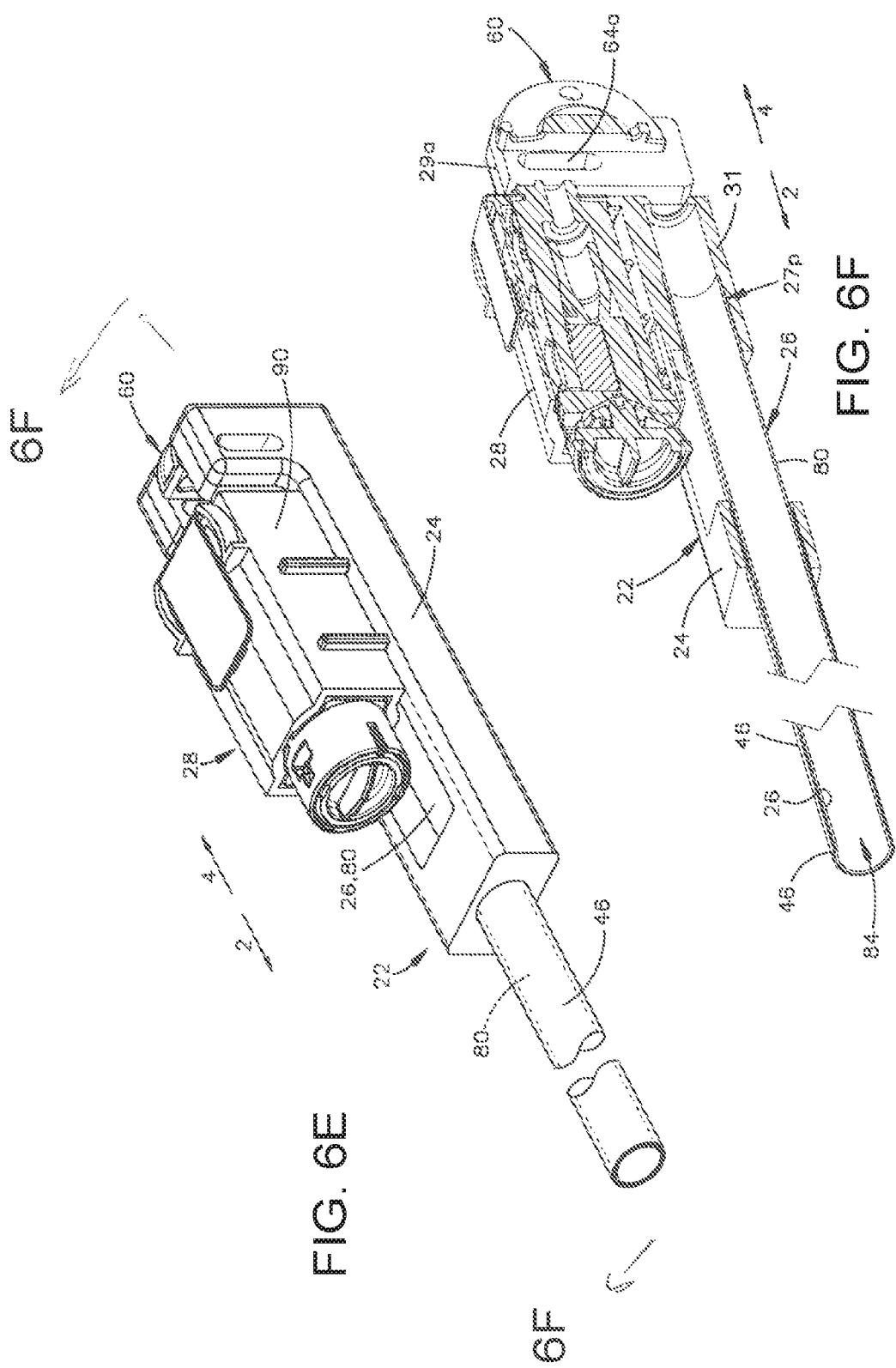

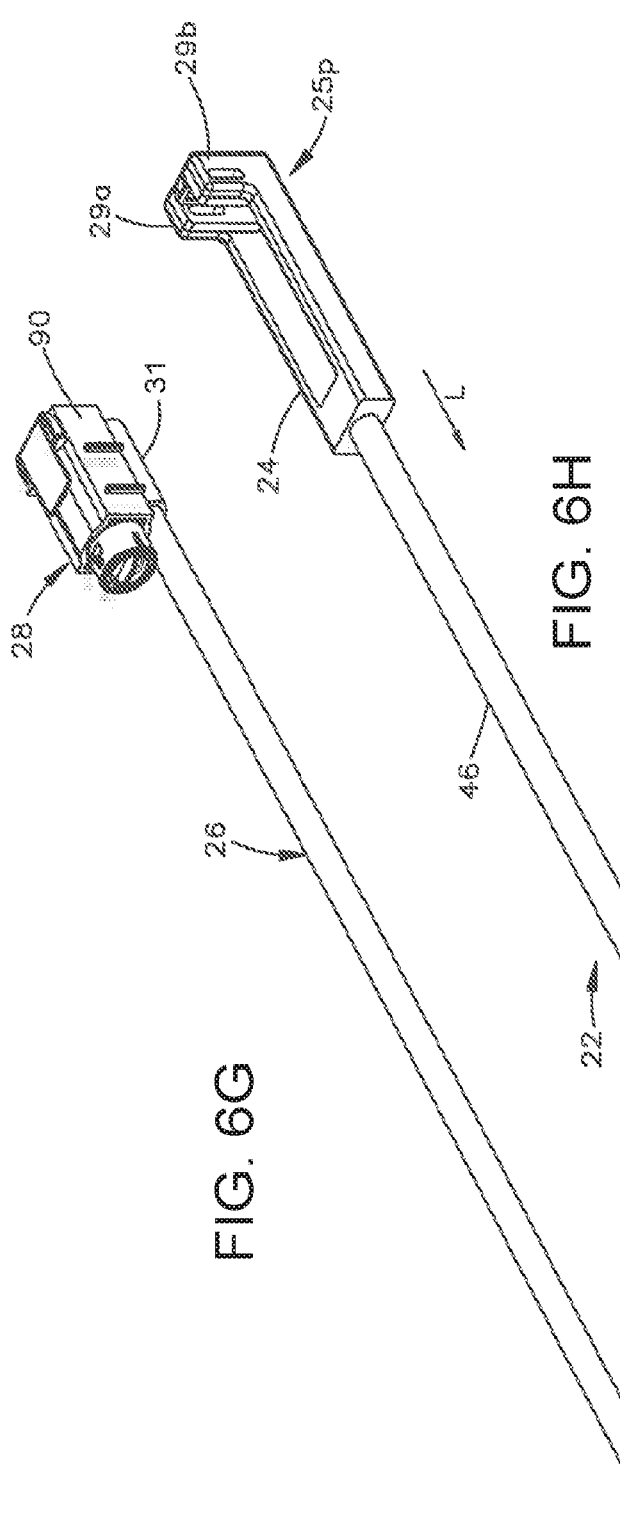

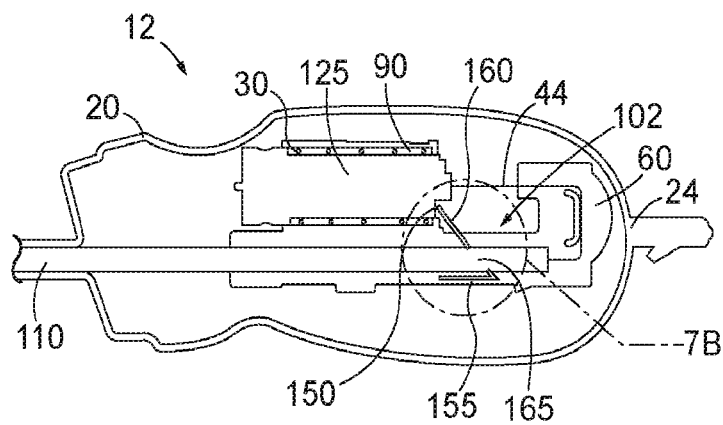 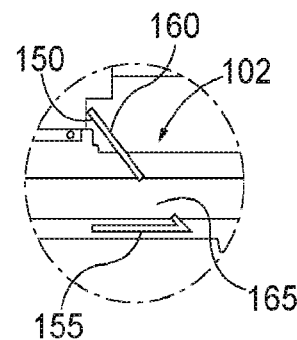
FIG. 7A    FIG. 7B
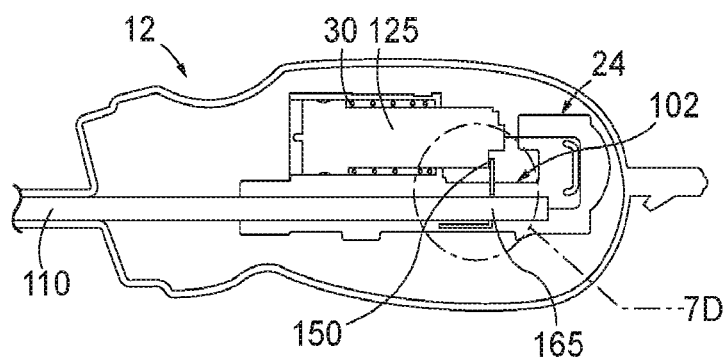 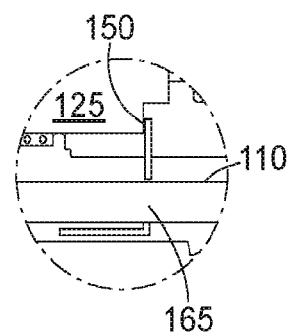
FIG. 7C    FIG. 7D
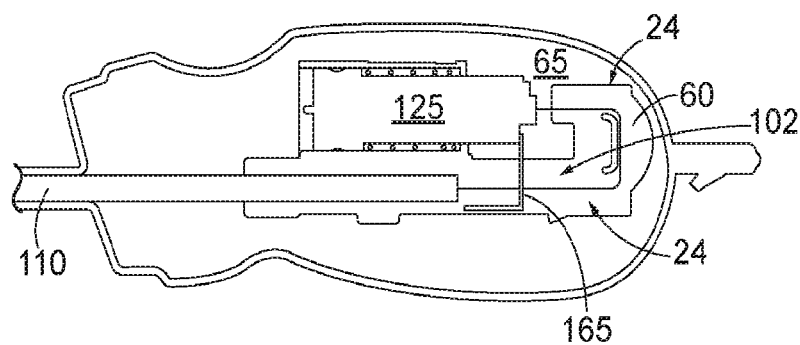
FIG. 7E

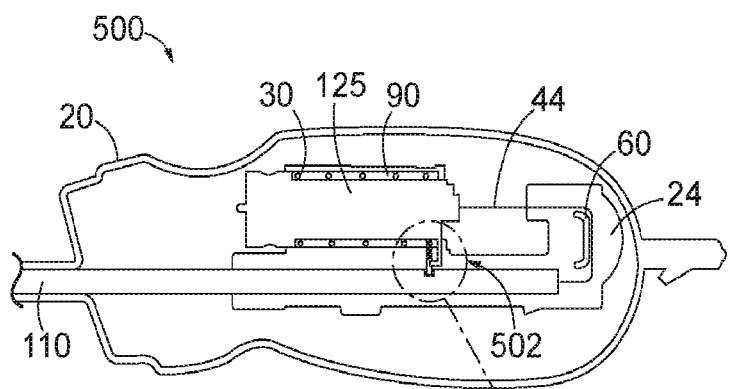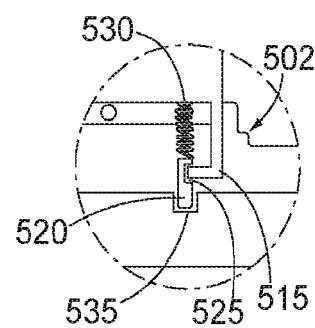
FIG. 10A  FIG. 10B
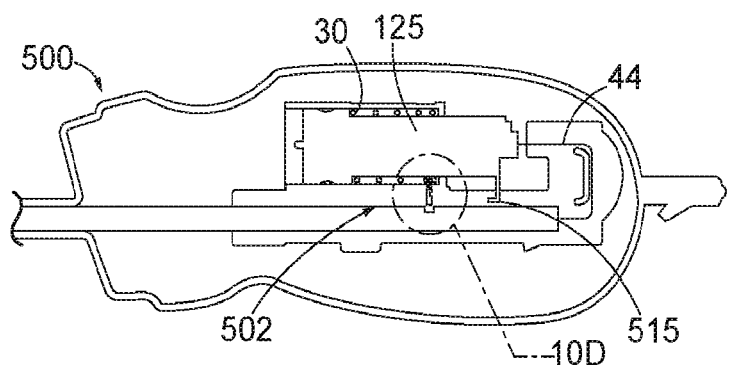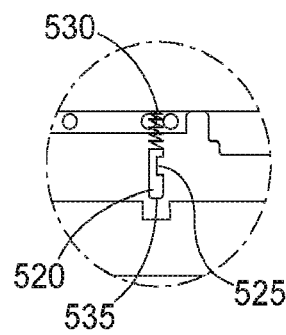
FIG. 10C  FIG. 10D
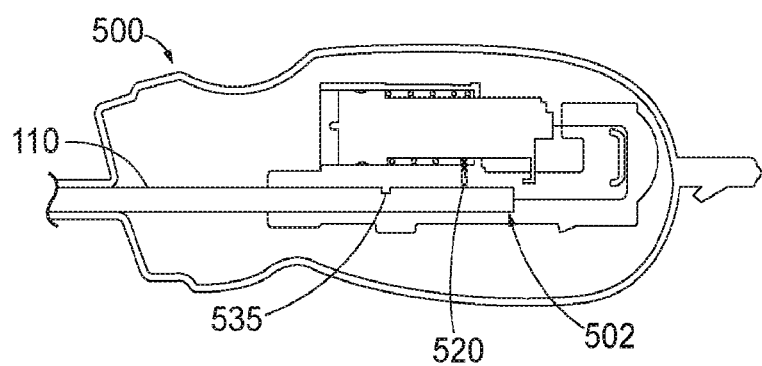
FIG. 10E

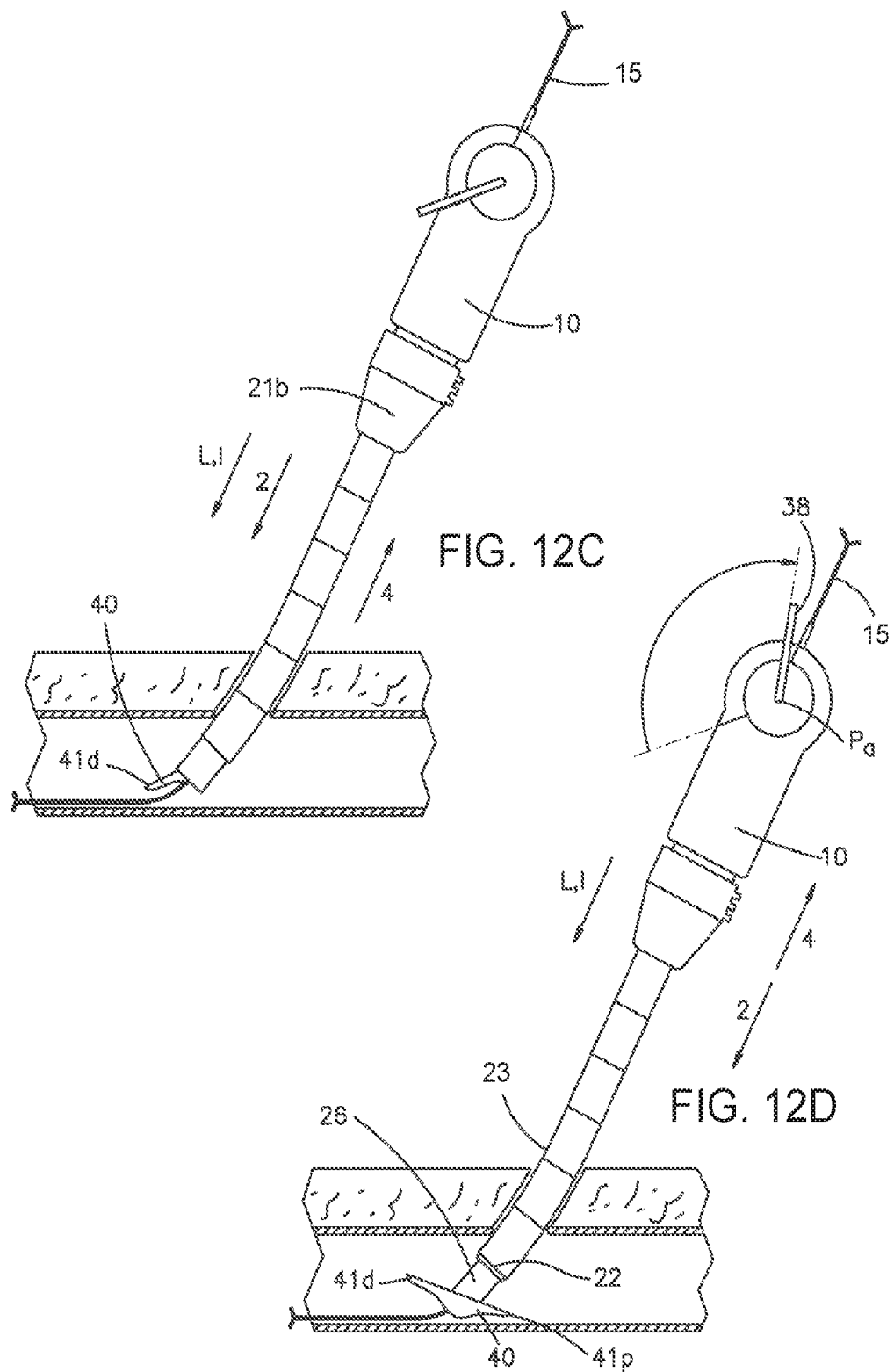

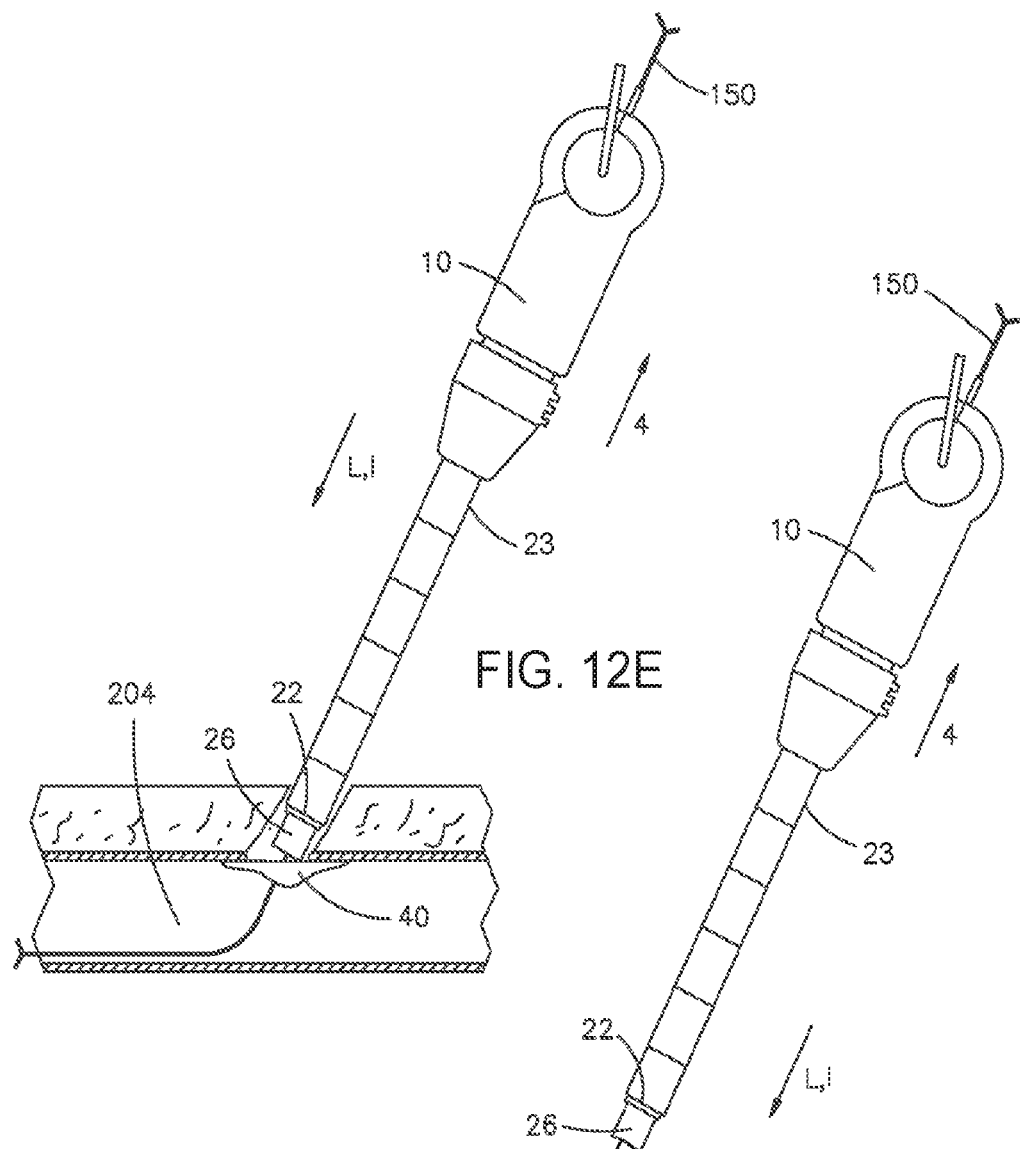

VASCULAR CLOSURE DEVICE WITH LOCKING ASSEMBLY FOR A TAMPER

CROSS-REFERENCE TO RELATED APPLICATIONS

The present application claims priority to and the benefit of U.S. Provisional Application Ser. No. 62/374,177, filed Aug. 12, 2016, the entire disclosure of which is incorporated by reference into the present application.

TECHNICAL FIELD

The present disclosure relates to a vascular closure device with a locking assembly for a tamper.

BACKGROUND

Percutaneous access of the vascular system for vascular device delivery is a common medical procedure. Typically this involves using a hollow needle to puncture a vessel, then introducing an introducer sheath to open the puncture site for the introduction of catheters and wire guides for navigation through the vascular system to facilitate delivery. For example, in many cases, vascular access requires introduction of catheters and wire guides through the femoral artery. Once the procedure is completed, the devices are removed from the patient and pressure is applied to the puncture site to stop the bleeding. Thereafter, the puncture may be sealed using a closure device. Closure devices generally consist of three basic sealing components: a toggle (or anchor) member, a sealing member, such as a plug, and a suture. To lock the components together within the puncture, a locking member may be used.

SUMMARY

A vascular closure device in accordance with an embodiment can include a deployment assembly that is elongate along a longitudinal direction and that has a distal end and a proximal end spaced from the distal end in a proximal direction that is aligned with the longitudinal direction. The vascular closure device includes a sealing unit carried by the deployment assembly. The sealing unit includes a suture coupled to the deployment assembly. The vascular closure device includes a tamper carried by the deployment assembly and that is disposed along the suture with respect to the sealing unit in the proximal direction. The tamper includes a lumen that receives the suture such that the tamper is slidable along the suture. The vascular closure device includes a locking assembly coupled to the tamper so as to selectively inhibit advancement of the tamper along the suture in the distal direction toward the sealing unit. The locking assembly is adapted to transition from A) a locked configuration where the tamper is inhibited from sliding along the suture, into B) an unlocked configuration where the tamper is slidable along the suture in the distal direction and into contact with the sealing unit.

BRIEF DESCRIPTION OF THE DRAWINGS

The foregoing summary, as well as the following detailed description of an example embodiment of the application, will be better understood when read in conjunction with the appended drawings. The drawings show exemplary embodiments for the purposes of illustration. It should be understood, however, that the application is not limited to the precise arrangements, scale, and systems as shown. In the drawings:

FIG. 2 is a perspective view of the vascular closure device shown in FIG. 1, including a sealing unit;

FIG. 3 is a partial cut-away view of the vascular closure device shown in FIG. 2;

FIGS. 6A-6C are rear perspective views of the vascular closure device with portions of the device removed for clarity;

FIG. 6E is a perspective view of the release component, delivery component and tension element of the vascular closure device shown in FIG. 6A;

FIG. 6F is a perspective cross-sectional view of the release component, delivery component and the tension element of the vascular closure device shown in FIG. 6E, taken along line 6F-6F;

FIG. 6G is a perspective view of the delivery component and tension element of the vascular closure device shown in FIG. 6E;

FIGS. 6H and 6I are perspective and top views, respectively, of the release component of the vascular closure device shown in FIG. 5;

FIGS. 7A-7E are partial sectional views of the vascular closure device shown in FIG. 6A, illustrating the tension element, a locking assembly and the tamper;

FIGS. 10A-10E are partial sectional views of a vascular closure device according to another embodiment, illustrating a tension element, a locking assembly and a tamper;

FIGS. 12A-12I are schematic sectional views illustrating a method by which the vascular closure device is used to seal a puncture in an artery.

DETAILED DESCRIPTION OF ILLUSTRATIVE EMBODIMENTS

Figure 1:
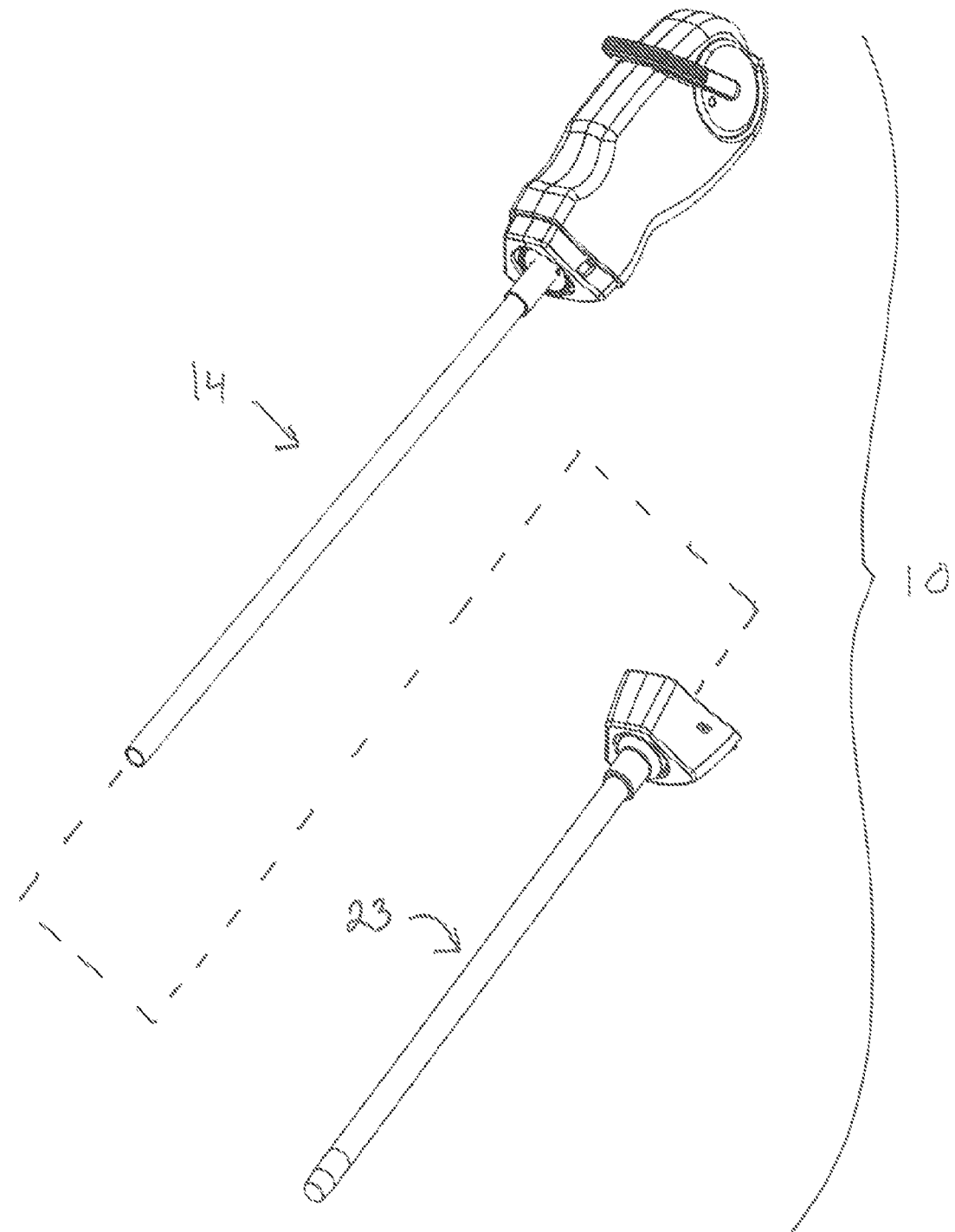
FIG. 1 is a perspective view of the vascular closure device and access sheath of a vascular closure system in accordance with an embodiment of the present disclosure.

Certain terminology is used in the following description for convenience only and is not limiting. The words "right", "left", "lower" and "upper" designate directions in the drawings to which reference is made. The words "proximally" and "distally" refer to directions toward and away from, respectively, the individual operating the system. The terminology includes the above-listed words, derivatives thereof and words of similar import.

Referring to FIGS. 1-3, embodiments of the present disclosure include a puncture closure system 10 used to seal puncture in an arterial wall. The puncture closure system 10 includes an introducer (not shown), such as a dilator, and a vascular closure device 12 that is configured to seal the puncture in an arterial wall. The vascular closure device 12 includes a sealing device 18, a deployment assembly 14 that releasably carries the sealing device 18, and an access sheath 23. The access sheath 23 can be inserted into the puncture along a guidewire 15 (FIG. 12A) and over the introducer to form an insertion assembly. After the introducer is removed from the access sheath 23, the deployment assembly 14 can be inserted into, and coupled with, the access sheath 23 to position the sealing device 18 (FIG. 12B) in the artery.

Figure 4:
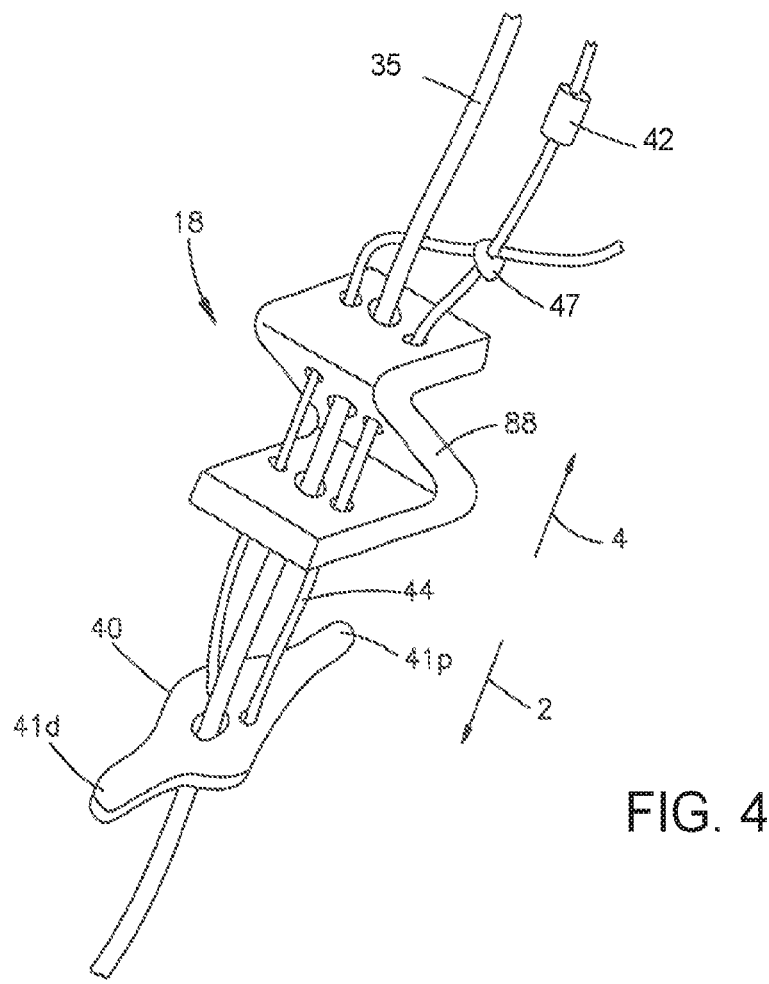
FIG. 4 is a perspective view of the sealing device in the vascular closure device illustrated in FIGS. 2 and 3.
Figure 5:
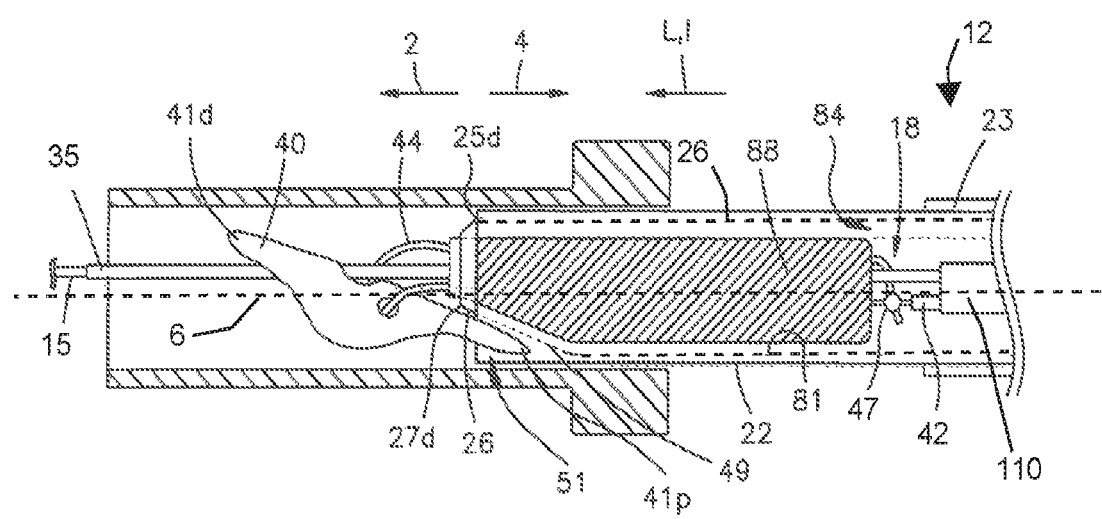
FIG. 5 is a detailed sectional view of a distal portion of the vascular closure device shown in FIG. 1-4.

Turning to FIGS. 4 and 5, the vascular closure device 12 includes a sealing device 18 and a tamper 110 at least partially disposed within a deployment assembly 14. The sealing device 18, which may be referred to as an implantable unit, includes a toggle 40, a suture 44 coupled to the toggle 40, a plug 88 coupled to the suture 44 and spaced from the toggle 40 in a proximal direction 4, and a locking member 42 disposed on the suture 44 proximal to the plug 88. The vascular closure device 12 is configured such that after a distal portion of deployment assembly 14 is inserted through the puncture site of the vessel, the sealing device 18 can be deployed to seal or otherwise close the puncture site. The deployment assembly 14 controls orientation of the toggle 40 as the sealing device 18 is advanced through the access sheath 23 in an easier and more efficient manner. Furthermore, the deployment assembly 14 is also configured to reduce forces required to deploy the sealing device 18 and seal the puncture.

Referring to FIGS. 4 and 5, the toggle 40 includes a distal end 41d, a proximal end 41p opposite to the proximal end 41p, and a plurality of apertures (not numbered) extending therethrough. The suture 44 extends through the apertures as illustrated such that an end of the suture 44 is formed into a slidable knot 37. The knot 37 is slidable along the suture 44 between the plug 88 and the locking member 32. In an implanted state, the toggle 40 is adjacent to an inner surface of the vessel and the locking member 32 squeezes the toggle 40 and the plug 88 against the vessel to seal the puncture.

The sealing device 18 is formed with materials suitable for surgical procedures. The toggle 40 can be made of any biocompatible material. For example, the toggle 40 can be made of a polylactic-coglycolic acid or other synthetic absorbable polymer that degrades in the presence of water into naturally occurring metabolites. In other embodiments, the toggle 40 can be made of stainless steel, biocorrodible iron, and biocorrodible magnesium. It should be appreciated, however, that the toggle 40 can be made of other materials and can have other configurations so long as it can be seated inside the vessel against the vessel wall. The plug 88 can comprise a strip of compressible, resorbable, collagen foam and can be made of a fibrous collagen mix of insoluble and soluble collagen that is cross linked for strength. It should be appreciated, however, that the plug member 88 can have any configuration as desired and can be made from any material as desired. The suture 44 can be any elongate member, such as, for example a filament, thread, or braid.

The vascular closure devices includes a tamper 110 disposed along the suture 44 in a proximal direction with respect to the locking member 42. The tamper 110 includes a first lumen that receives the suture 44 therethrough and a second lumen that receives the guide member 35. The tamper 110 is selectively slideable along the suture 44 to tamp the locking member 42 into a compressed plug so as to seal the puncture. In accordance with the present disclosure, the vascular closure device 12 includes a locking assembly 102 that is used to lock the tamper 110 in place until a threshold level of tension is applied to the suture 44.

After the requisite tension is applied, the locking assembly is unlocked and the tamper 110 can be advanced along the suture 44 to tamp the locking member 42 into position on the plug 88. The locking assembly will be further described below.

Referring to FIGS. 2 and 3, the deployment assembly 14 includes a handle member 20, a release component 22, a delivery component 26 that contains at least a portion of the toggle 40, a tension element 28, a guide member 35, and one or more actuators 38 coupled to the release component 22. The toggle 40 is trapped between the release component 22 and the delivery component 26 as shown in FIG. 5. The guide member 35 extends through the sealing device 18, such as the plug 88 and toggle 40, and is configured to receive a guidewire 15 as will be discussed below. In another example, the deployment assembly 14 can be configured so that the guidewire 15 extends along the side of the toggle 40. The release component 22 is operatively associated with the suture 44 such that actuation of the actuator 38 causes the release component 22 to 1) release the toggle 40, and 2) apply tension to the suture 44, which urges the toggle 40 against the delivery component 26 and orients the toggle 40 in the sealing position. The guide member 35 is configured to be removed from at least the sealing device 18 prior to the sealing device 18 sealing the puncture.

Referring again to FIGS. 2 and 3, the deployment assembly 14 is elongate along a longitudinal direction L and includes a rear end 16p and a front end 16d spaced from the rear end 16p along an axis 6 that is aligned with the longitudinal direction L. The longitudinal direction L can include and define a distal direction 2 that extends from the rear end 16p toward the front end 16d. Further, the longitudinal direction L can include and define a proximal direction 4 that is opposite the distal direction 2 and that extends from front end 16d toward the rear end 16p. The deployment assembly 14 is configured to insert the toggle 40 into the vessel along an insertion direction I. The longitudinal direction L can be aligned with the insertion direction I during a portion of the sealing procedure.

Referring to FIGS. 2 and 3, in accordance with the illustrated embodiment, the deployment assembly 14 includes a handle member 20. The handle member 20 includes a housing 21a and a cavity 21c defined at least partly by a housing 21a and a hub 21b of the access sheath 23. The cavity 21c is sized to contain a portion of the release component 22, the delivery component 26, and the tension element 28. As shown, the handle member 20 supports the release component 22 such that the release component 22 extends from the handle member 20 in the distal direction 2. The delivery component 26 also supported by the handle member 20 and extends along the distal direction 2 within a lumen of the release component 22. The tension element 28 is contained in the housing 21a coupled to a proximal end of the release component 22. A portion of delivery component 26 is shown in dashed lines in FIGS. 2 and 3.

The actuator 38 is coupled to both the handle member 20 and the release component 22. As noted above, the actuator 38 is configured to 1) cause the release component 22 to move in the proximal direction 4 from a first or initial position relative to the delivery component 26 into a second or release position relative to the delivery component 26, and 2) apply a tensile force to the suture 44 during or subsequent to movement of the release component 22 from the initial position into the released position. The description below refers to the release component 22 being moveable relative to the delivery component 26. But the deployment assembly 14 can be configured so that the delivery component 26 is moveable relative to the release component 22.

Turning to FIGS. 6H and 6I, the release component 22 is elongate along a first or longitudinal direction L. The release component 22 defines a distal end 25*d* and a proximal end 25*p* spaced from the distal end 25*d* along the longitudinal direction L. In accordance with the illustrated embodiment, the release component 22 includes a hub 24 and a release tube 46 that is fixed to the hub 24 and that extends from the hub 24 in the distal direction 2. The hub 24 is disposed at the proximal end 25*p* of the release component 22. As illustrated, the release hub 24 includes a pair of tabs 29*a*, 29*b*, and a pulley 60 coupled to and disposed between the tabs 29*a*, 29*b*. The pulley 60 defines a curved track that receives the suture 44 as will be explained below. The hub 24 defines a slot 47 that is elongate along the longitudinal direction L and is aligned with the release tube 46. The slot 47 is sized to receive a coupler 31 of the tension element 28.

Figure 6D:
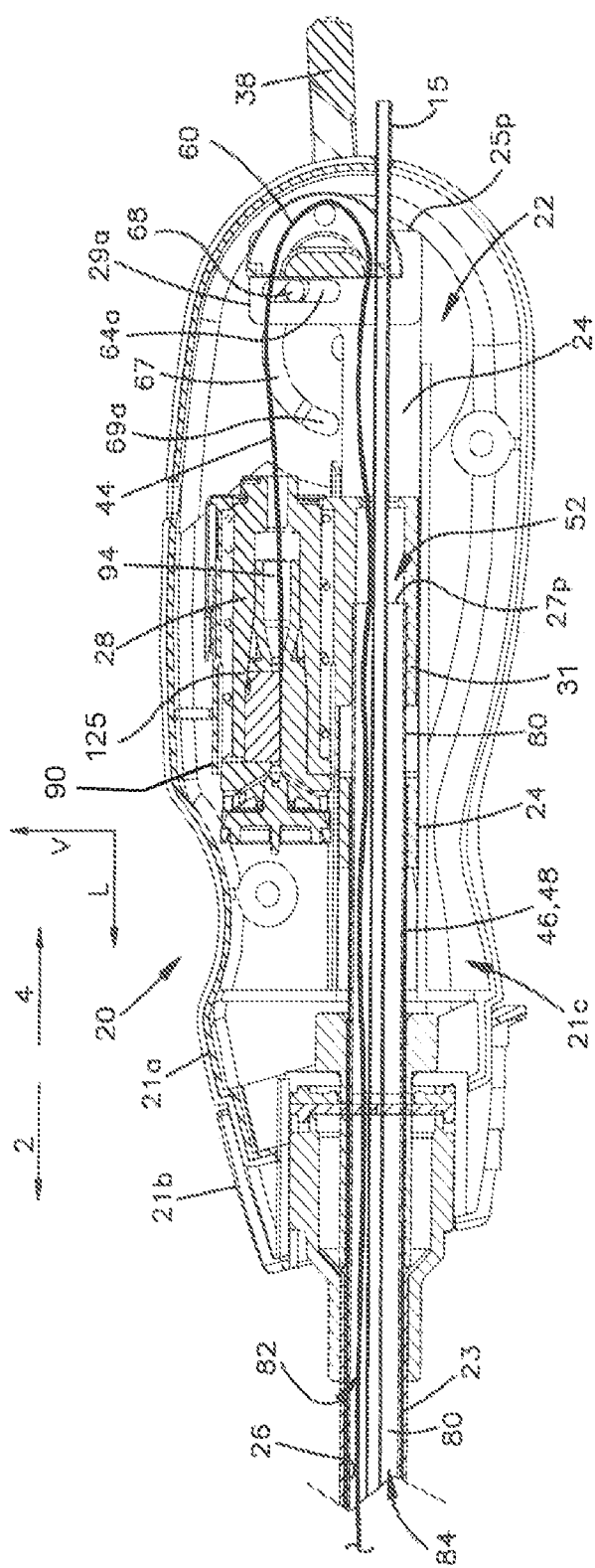
FIG. 6D is a sectional view of the vascular closure device shown in FIG. 6A.
Figure 8A:
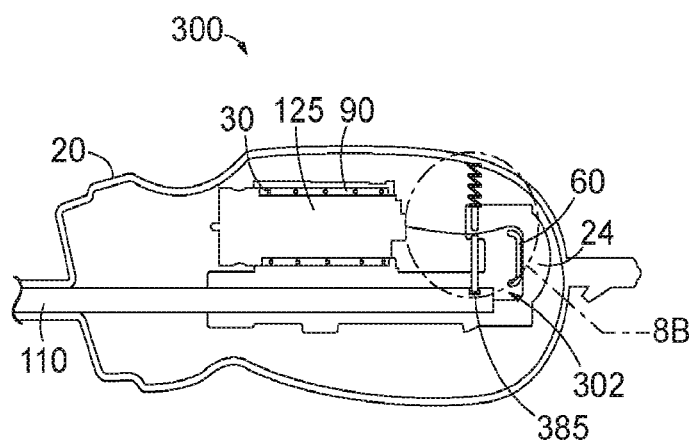
FIGS. 8A-8E are partial sectional views of the vascular closure device according to another embodiment, illustrating a tension element, a locking assembly and a tamper.
Figure 8B:
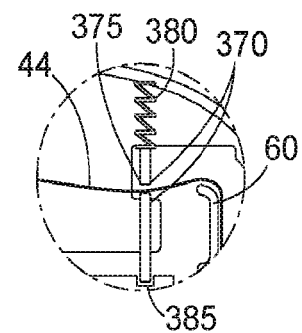
Figure 8C:
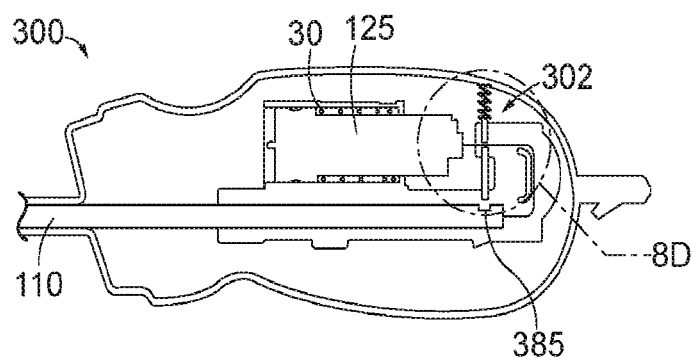
Figure 8D:
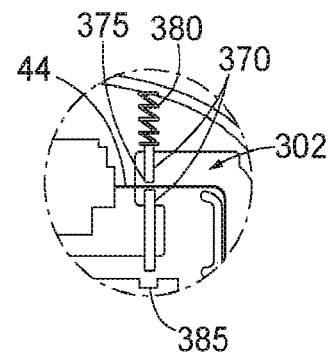
Figure 8E:
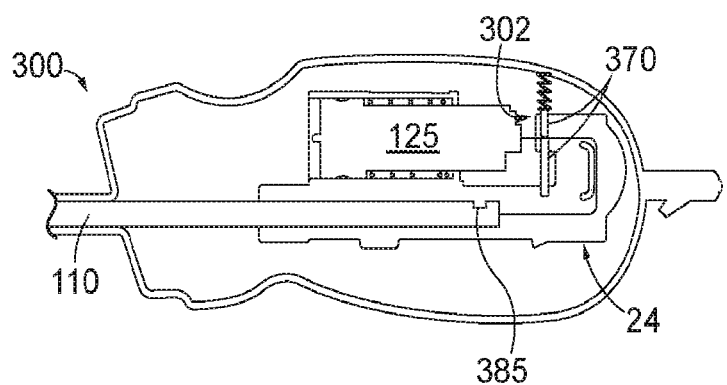

Referring to FIGS. 6H and 6I, the release tube 46 includes a release tube body that is elongate along the longitudinal direction L. The release tube body defines a release tube channel 52 (FIG. 6D) that extends along the longitudinal direction L from the hub 24 toward the distal end 25*d*. In the illustrated embodiment, the release tube channel 52 extends completely through the release tube body from the hub 24 to the distal end 25*d*. The release tube body is cylindrical such that the release tube channel 52 is radially enclosed. It should be appreciated, however, that the release tube channel 52 can extend partially through the release tube body as desired and that the release tube body can have other configurations as desired. For example, the release tube body can be U-shaped such that the release tube channel 52 is partially radially open. As shown, the release tube channel 52 is sized to slidably receive a portion of the delivery component 26 such that the release component 22 is movable relative to the delivery component 26. As shown in FIG. 6D, the suture 44 extends around the pulley 60 along the guide track and into the tension element 28. As the release component 22 is pulled in the proximal direction 4, the pulley 60 pulls the suture 44 in proximal direction 4 thereby applying a tensile force to the toggle 40. In such an embodiment, the tension element 28 is positioned alongside the release component 22. It should be appreciated, however, that in some embodiments, the tension element 28 is positioned proximal to the release tube and is in-line with the release component 22 such that the suture 44 extends through the release tube 46 and into the tension element 28 along the first direction L.

With continued reference to 6A, 6B, and 6D, the release component 22 can be operatively coupled to the actuator 38. The release component 22 includes at least one mating member 64*a*, 64*b* that mates with a corresponding mating member 68 of the actuator 38. The mating members 64*a*, 64*b* and 68 are engaged with other so to transfer the motion of the actuator 38 to the release component 22. In the illustrated embodiment, the release component mating member 64 is a pair of slots 64*a* and 64*b* defined by the respective pair of tabs 29*a* and 29*b* of the hub 24. Each slot 64*a* and 64*b* is elongate along a vertical direction V that is perpendicular to the longitudinal direction L. The mating member 68, which can be a pin, is disposed inside the slots 64*a* and 64*b* such that actuation of the actuator 38 causes the release component 22 to translate along the longitudinal direction L. It should be appreciated, however, that the mating member 64*a*, 64*b* can have any configuration as desired. For example, the mating member 64*a*, 64*b* can be a bore having a diameter that is equal to that of the pin such that translation of the actuator 38 causes the release component 22 to translate along the first direction L.

As shown in FIGS. 6D-6G, the delivery component 26 is coupled to the tension element 28 and extends along the release component 22 toward the front end 16*d* of the deployment assembly 14. In accordance with the illustrated embodiment, because the tension element 28 is fixed to the housing 21*a*, the delivery component 26 is fixed to the housing 21*a* and thus the handle member 20. The delivery component 26 includes a delivery tube body 80 that is elongate along the direction L and defines a distal end 27*d* and a proximal end 27*p* spaced from the distal end 27*d* in the direction L. The delivery tube body 80 defines an inner surface 81, which in turns defines a delivery tube channel 84 that extends at least partially through the delivery tube body 80 along the first direction L. As illustrated embodiment, the delivery tube channel 84 extends completely through the delivery tube body 80 from the proximal end 27*p* to the distal end 27*d*. However, the channel 84 can extend along a portion of the delivery tube body 80. In the illustrated embodiment, the delivery tube body 80 is cylindrical such that the delivery tube channel 84 is radially enclosed. It should be appreciated, however, that the delivery tube channel 84 can extend partially through the delivery tube body 80 as desired and that the delivery tube body 80 can have other configurations as desired. For example, the delivery tube body 80 can be U-shaped such that the delivery tube channel 84 is partially radially open. As illustrated, the proximal end 27*p* of the delivery component is fixed to the tension element 28. The distal end 27*d* of the delivery component is configured to hold at least a portion of the sealing device 18 (FIG. 4).

Referring to FIG. 5, the deployment assembly 14 releasably carries at least a portion of the sealing device 18. In particular, the plug 88 and locking member 32 are retained within the delivery tube channel 84, while the toggle 40 is configured to be initially trapped between the delivery component 26 and the release component 22. As shown, the distal end 25*d* of the release tube 48 defines an offset surface 49, which can be angled with respect to the longitudinal axis 6. The offset surface 49 and inner surface 81 of the delivery tube body 80 define a cavity 51 that receives the proximal end 41*p* of the toggle 40 when the release component 22 is in the initial position. The angle of the offset surface 49 can define the orientation of the toggle 40 in this initial position, whereby the distal end 41*d* of the toggle 40 is spaced some distance in the distal direction 2 beyond the distal ends 25*d* and 27*d* of the release component 22 and delivery component 26, respectively. The suture 44 extends from the toggle 40 through the delivery tube channel 84, through the proximal end 27*p* around the pulley 60 along the guide track and is coupled to the tension element 28 (FIG. 6D). The guide member 35 extends through the channel 84 and exits the front end 16*d* of the vascular closure device 12.

When the actuator 38 is actuated as will be further detailed below, the release component 22 moves in the proximal direction 4 thereby releasing the proximal end 41*p* of the toggle 40 from between the release component 22 and the delivery component 26. As the release component 22 moves in the proximal direction 4, the suture 44 will be pulled in the proximal direction 4 to thereby place the suture 44 in tension and urge the toggle 40 against the distal end 27*d* of the delivery component 26. At this point, the toggle 40 is oriented in the sealing position (see FIG. 12D). In the sealing position, the toggle 40 has been repositioned so that the toggle 40 is placed against the distal end 27*d* of the delivery component 26 and is oriented more transversely with respect to the axis 6 compared to the position when the toggle 40 is restrained by the release component 22.

As shown in FIGS. 6D-6G, the tension element 28 is disposed on the delivery component 26 and receives the suture 44 as noted above. In accordance with the illustrated embodiment, the tension element 28 includes a tension element housing 90, a cartridge 125 disposed with the housing 90, and a spring 31 between the housing 90 and the cartridge 125. The tension element 28 also includes a coupler 31 that extends from the housing 90 and is attached to the delivery component 26, and a drag member 94 disposed within the tension element housing 90. The suture 44 extends into the tension element housing 90 through the drag member 94 and is attached to the cartridge 125 such that a frictional force is applied to the suture 44 by the drag member 94. The tension element housing 90 is fixed to the housing 21a. The cartridge 125 can move with respect to the housing 90. The coupler 31 as illustrated is a tubular component that receives the proximal end 27p of the delivery tube body 80. As illustrated, the delivery tube body 80 is fixed to the coupler 31 which indirectly fixes the delivery component 26 to the housing 21a.

The suture 44 is spooled within the tension element housing 90 (not shown). Spooling the suture 44 in tension element housing 90 allows suture 44 to dispense from the deployment assembly 14 when the deployment assembly 14 is pulled in the proximal direction 4 to thereby deploy the sealing device 18 from the deployment assembly 14. The frictional force applied to the suture 44 by the drag member 94 can be high enough to maintain the suture 44 in tension after the actuator 38 has been actuated and the toggle 40 has been urged against the distal end 27d of the delivery component 26. At the same time the frictional force applied to the suture 44 by the drag member 94 can be low enough to allow the suture 44 to dispense from the tension element housing 90 when the deployment assembly 14 is pulled in the proximal direction 4 relative to the toggle 40. In the illustrated embodiment, the drag member 94 is a silicon member that pinches the suture 44. The tension element housing 90 and drag member 94 can be similar to the tension element described in U.S. Patent Application Publication No. 2013/0178895. It should be appreciated, however, that the drag member 94 can have other configurations as desired.

Turning to FIGS. 6A-6D, the deployment assembly 14 can include one or more actuators that are configured to transition the release component 22 into to releasing position and to cause a tension to be applied to suture 44 when the toggle 40 is released. In accordance with the illustrated embodiment, the actuator 38 can be configured as a lever that is rotatably coupled to the handle member 20. Rotation of the lever can cause the release component to translate as to release the toggle 40.

As illustrated in FIGS. 6A-6D, the actuator 38 or lever can include a pair of side mem that connects the first leg 37a to the second leg 37b. The actuator 38 is configured to pivot about a pivot axis $A_P$ that is perpendicular to the axis 6. The pivot axis $A_P$ may or may not intersect axis 6. The housing 21a defines a pair of curved housing slots 67 that are curved with respect to the pivot axis $A_P$. Only one curved slot 67 is shown in the Figures and is described below for illustrative purposes. The curved slots 67 are substantially similar to each other. The curved housing slot 67 has a first end 69a (FIG. 6D) and second end (not numbered) spaced apart from the first end along the proximal direction 4. The mating member 68 of the actuator 38 can be a pin 68 that is coupled to and extends between the side members 71 and 71b at a location that is offset from the pivot axis $A_P$. The pin 68 extends through the curved housing slot 67 and through the elongate slots 64a and 64b of the hub 24 of the release component 22 such that the actuator 38 is operatively coupled to the release component 22.

In use, as the actuator 38 pivots about the pivot axis $A_P$, the pin 68 moves from the first end 69a of the curved housing slots 67 toward the second end of the curved housing slots 67, and also moves along the slots 64a and 64b along the vertical direction V. Because the release component 22 is moveable relative to housing 21a, as the pin 68 moves along the curved housing slots 67, the pin 68 advances the hub 24 of the release component 22 in the proximal direction 4. The result in accordance with the illustrated embodiment is that rotation of the actuator 38 causes the release component 22 to translate in the longitudinal direction L. It should be appreciated, however, that the actuator 38 can have other configurations as desired and is not limited to the disclosed lever.

In operation, the deployment assembly 14 is initially configured to insert the toggle 40 into the vessel. When the actuator 38 is actuated, the release component 22 moves in the proximal direction 4 relative to the delivery component 26 into the releasing position (not illustrated) thereby releasing the proximal end 41p of the toggle 40 from between the release component 22 and the delivery component 26. As the release component 22 moves in the proximal direction 4, the suture 44 will be pulled in the proximal direction 4 to thereby place the suture 44 in tension and urge the toggle 40 against the distal end 27d of the delivery component 26. At this point, the toggle 40 is oriented in the sealing position (see FIG. 12D). Accordingly, the release component 22 is configured to restrain the toggle 40 of the sealing device 18 during insertion of the vascular closure device 12 into the vessel and subsequently release the toggle 40 so that the toggle 40 can be oriented for the sealing procedure.

Furthermore, when the actuator 38 is actuated, the release component 22 pulls the suture 44 in the proximal direction to thereby place the suture 44 in tension. Application of tension along the suture 44 urges the toggle 40 against the distal end 27d of the delivery component 26 and orients the toggle 40 into the sealing position. In the illustrated embodiment, the actuator 38 and release component 22 are configured such that continuous movement of the actuator 38 relative to the housing 21a will move the release component 22 in the proximal direction 4, thereby releasing the toggle 40 from the release component 22 and subsequently apply tension to the suture 44. It should be appreciated, however, that in some embodiments the suture 44 can be tensioned as the toggle 40 is being released. It should further be appreciated that in some embodiments, the deployment assembly 14 can include a first actuator to release the toggle 40 and a second actuator that tensions the suture 44.

The release component 22 and delivery components 26 are described above has having tubular shaped bodies. It should be appreciated that the release and delivery components can have other configurations. For instance, the release component can be elongate rod, or an elongate rod with a tubular ring coupled to its distal end. The delivery component can be configured such that only a portion thereof has a tubular shape.

Referring to FIGS. 1-3, the deployment assembly 14 described above is inserted into and coupled to the access sheath 23. The access sheath 23 is elongate along a longitudinal direction L. The access sheath 23 defines a distal end $D_A$, a proximal end $P_A$, and an access channel 36 that extends from the proximal end $P_A$ to the distal end $D_A$ along the longitudinal direction L. The access sheath 23 also includes a hub 21b and a shaft 21d that extends from the hub 21b. The proximal end, which can be referred to as the rearward end, of the access sheath includes the hub 21b that is configured to be coupled to a portion of the deployment assembly 14. When the sheath 23 is coupled to the deployment assembly, the shaft 21d extends along the release component 22 and delivery component 26 in a distal direction 2.

The vascular closure device 12 as described herein also includes a locking assembly coupled to the tamper 110 so as to selectively inhibit advancement of the tamper 110 along the suture 44. The locking assembly is adapted to transition from A) a locked configuration where the tamper 110 is inhibited from sliding along the suture, into B) an unlocked configuration where the tamper 110 is slidable along the suture 44 in the distal direction and into contact with the sealing device 18. FIGS. 7A-11C illustrate various embodiments of a locking assembly used to control the tamper 110.

Referring to FIGS. 7A-7E, the vascular closure device 12 includes a locking assembly 102 used to control release of the tamper 110 during use. The locking assembly 102 is operatively coupled to the tension element 28 so that, in response to the level of tension applied to the suture 44, the locking assembly transitions between the locked configuration and the unlocked configuration. As illustrated, the suture 44 is attached to a tension cartridge 125 and passes around a pulley 60 into a distal end of the tamper 110 toward the sealing device 18. As described above, the tension element 28 includes the housing 90, a tension cartridge 125, a compression spring 30 that fits between the tension cartridge 125 and the housing 90. The locking assembly 100 includes a biasing plate 160 that is coupled to the cartridge 125 and the hub 24. A rearward surface on the tension cartridge 125 bears against the upper leg 150 of the plate 160. A fixed leg 155 of the spring plate 160 is rigidly attached to the hub 24. In a locked configuration, as shown in FIGS. 7A and 7B, the legs 150 and 155 of the spring plate 160 are at an acute angle with respect to each other. The tamper 110 extends along the suture 44 and passes through an opening 165 in the plate 160. The opening in the plate 165 has about the same cross-sectional dimension as the tamper 110. The angle of the upper leg 150 of the spring plate 160 causes the surfaces defining the opening 165 to abut the tamper 110, inhibiting movement of the tamper 110.

As shown in FIGS. 7C-7E, when tension is applied to the suture 44, the tension cartridge 125 is moved rearward compressing spring 30. The upper leg 150 of the spring plate 160 is pushed rearward by the rearward facing surface of the cartridge 125 until the angle between the upper leg 150 of the spring plate 160 and the fixed lower leg 155 of the plate 160 are at a proper angle, releasing the grip of the plate 160 on the tamper 110. The tamper 110 can then be moved forward through the opening 165.

Another embodiment of a vascular closure device 300 and locking assembly is shown in FIGS. 8A-8E. In accordance with an alternative embodiment, a vascular closure device 300 includes a locking assembly 302. The vascular closure device 300 is substantially similar to the vascular closure device 12 and the same reference numbers are used to refer to parts common to vascular closure device 12 and vascular closure device 300. The locking assembly 302 includes a slide pine 370 having an opening 375, and a biasing member 380. The biasing member 380 can be a compression spring 380. As illustrated, the suture 44 is attached to a tension cartridge 125 as described above. The suture 44 also passes through the opening 375 in a slide pin 370. A compression spring 380 applies a downward force on the slide pin 370 which, in turn, deflects the suture 44 in a downward direction. The slide pin 370 is deflected into a notch 385 of the tamper 110, which prevents the tamper 110 from moving along the longitudinal direction L. When tension is applied to the suture 44, the tension cartridge 125 is moved rearward compressing spring 30. Tension in the suture 44 applies an upward pressure on the slide pin 370, compressing the spring 380 and releasing the slide pin 370 from the notch 385. The tamper 110 can then be moved forward out of the device to tamp the locking member.

Figure 9A:
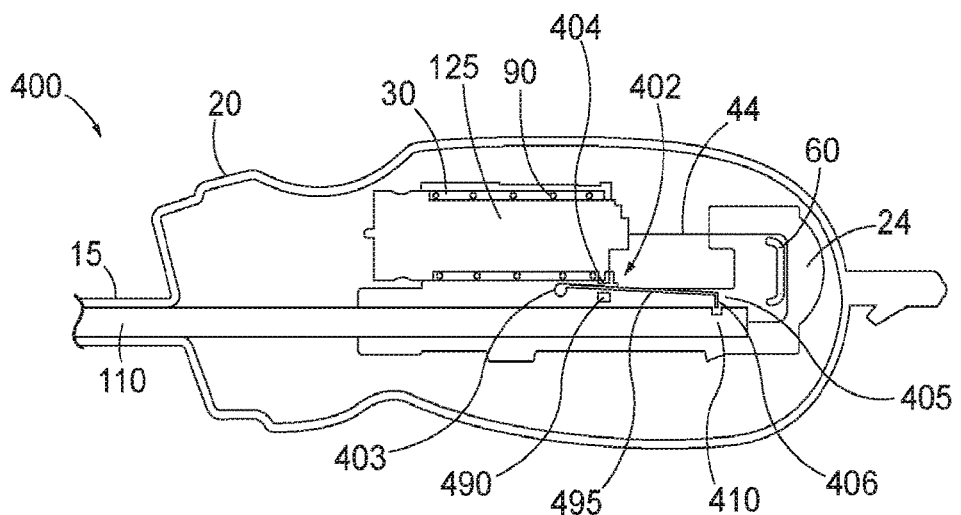
FIGS. 9A-9C are partial sectional views of a vascular closure device according to another embodiment, illustrating a tension element, a locking assembly and a tamper.
Figure 9B:
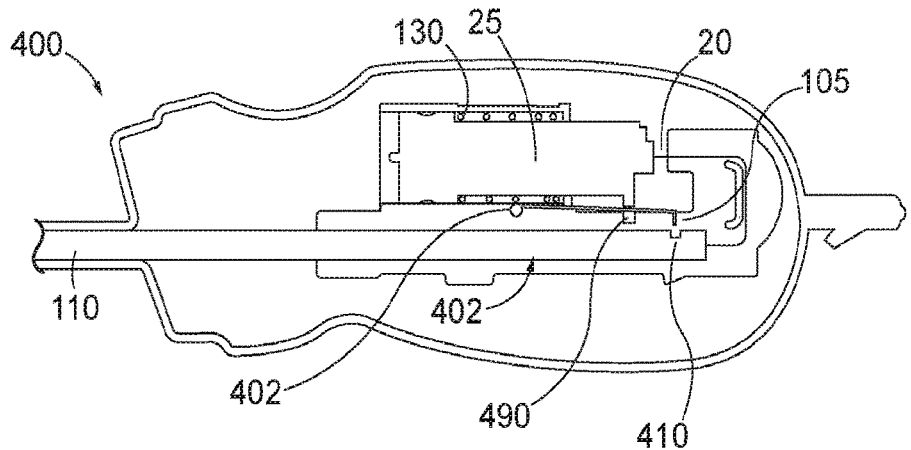
Figure 9C:
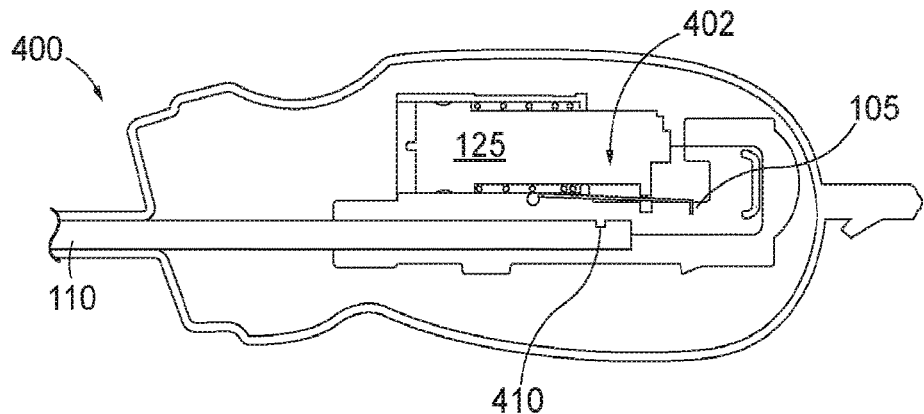

Another embodiment of a vascular closure device and locking assembly is shown in FIGS. 9A-9C. In accordance with an alternative embodiment, a vascular closure device 400 includes a locking assembly 402. The vascular closure device 400 is substantially similar to the vascular closure device 12 and the same reference numbers are used to refer to parts common to vascular closure device 12 and vascular closure device 400. As illustrated, a locking assembly 402 includes a lever 495 that includes a fixed or pivoting end 403 and a free end 405. The pivoting end 403 is pivotably fixed to the hub 24 of the release component 22. The lever 495 can therefore pivot about end 403. The free end 405 of the lever has a projection 406 that extends relative to the lever 495 at about a right angle. The suture 44 is attached to the tension cartridge 125. In accordance with the embodiment shown, the cartridge 125 includes a projecting tab 404 that defines an opening 490. The lever 495 passes through the opening 490. A tamper 110 extends along the suture 44. In an initial configuration, the free end 405 of the lever 495, e.g. the projection 406, engages a notch 410 in the tamper 110, which prevents the tamper 110 from moving along the longitudinal direction L. When tension is applied to the suture 44, the tension cartridge 125 is moved rearward compressing spring 30. Because the lever 495 passes through the opening 490 of the tab 404, as the cartridge 125 moves rearward, the opening 490 (i.e. the tab surface at the lower end of opening 490) rides along the lever 495 and lifts the free end 405 upwardly (as viewed in the figures). Movement of the free end 405 upwardly removes the projection 406 from the notch 410 in the tamper 110. The tamper 110 can then be moved forward.

Another embodiment of a vascular closure device and locking assembly is shown in FIGS. 10A-10E. In accordance with an alternative embodiment, a vascular closure device 500 includes a locking assembly 502. The vascular closure device 500 is substantially similar to the vascular closure device 12 and the same reference numbers are used to refer to parts common to vascular closure device 12 and vascular closure device 500. As illustrated, a locking assembly 502 includes an engagement tab 515, biasing member 530, and a slide pin 520. The engagement tab 515 is disposed on the rearward surface of the tension cartridge 125. The tab 515 can engage in the notch 525 in the slide pin 520, which fixes the position of the slide pin 520. The biasing member 530, which can be a tension spring, applies an upward force on the slide pin 520, urging the slide pin 520 toward the cartridge 125. The tamper 110 includes a notch 535 and the slide pin 520 engages the notch 535, which prevents the tamper 110 from moving along the longitudinal direction L. When tension is applied to the suture 44, the tension cartridge 125 is moved rearward releasing the engagement tab 515 from the notch 525 in the slide pin 520. The tension spring 530 pulls the slide pin 520 upward releasing it from the notch 535 in the tamper 110. The tamper 110 can then be moved forward as needed.

Figure 11A:
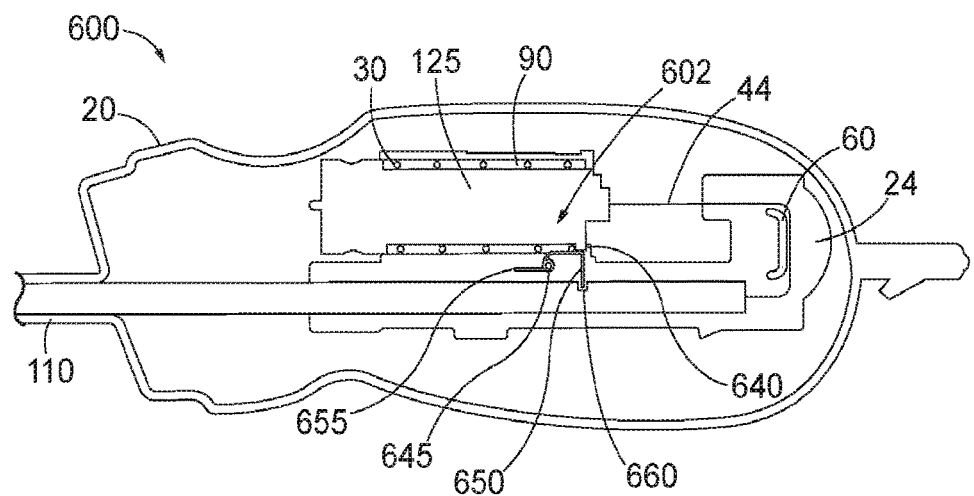
FIGS. 11A-11C are partial sectional views of the vascular closure device according to another embodiment, illustrating a tension element, a locking assembly and a tamper.
Figure 11B:
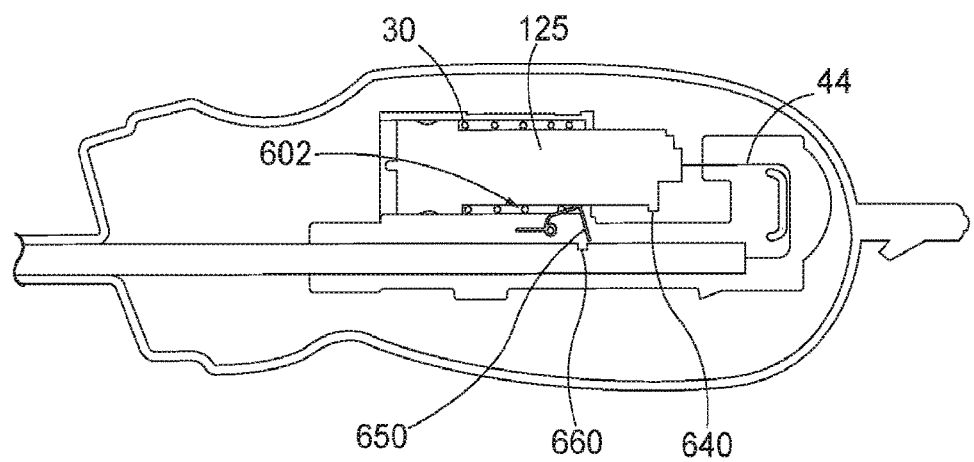
Figure 11C:
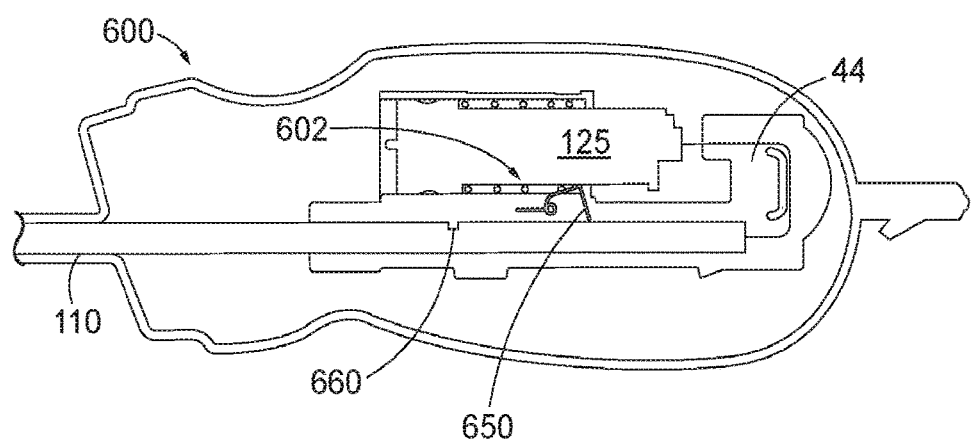

Another embodiment of a vascular closure device and locking assembly is shown in FIGS. 11A-11B. In accordance with an alternative embodiment, a vascular closure device 600 includes a locking assembly 602. The vascular closure device 600 is substantially similar to the vascular closure device 12 and the same reference numbers are used to refer to parts common to vascular closure device 12 and vascular closure device 600. As shown in FIGS. 11A-11B, the locking assembly 600 includes a torsion member 645. The torsion member 645 has a movable end 650, bent at a right angle, and a fixed end 655, attached to the hub 24. A protrusion 640 on the rearward surface of the tension cartridge 125 engages the movable end 650 of the torsion member 645, holding it in a downward position into engagement with the tamper 110. As illustrated, the moveable end 650 is captured by a notch 660 of the tamper 110, which prevents the tamper 110 from moving along the longitudinal direction L. When tension is applied to the suture 44, the tension cartridge 125 is moved rearward disengaging the protrusion 640 from the movable end 650 of the torsion member 650. The torsion member 650 rotates in a counter clockwise direction pulling the moveable end 650 out of the notch 660 in the tamper 110. The tamper 110 can then be moved forward, as needed.

Embodiments of the present technology will now be described with respect to exemplary large bore procedures that utilize the vascular closure system 10. In order to perform any of the related procedures, the user gains percutaneous access to, for example, the femoral artery, causing a puncture site in the artery. To gain percutaneous access to the artery, the Seldinger technique may be used. For example, a hollow bore needle is inserted into the artery. A guide wire 15 is then advanced through the hollow needle and into the femoral artery a sufficient distance to allow removal of the needle without the guide wire 15 pulling out of the vessel. Removing the needle leaves the guide wire 15 in place, with a portion of the guide wire 15 extending into the artery. The guide wire 15, extending from outside the patient into the femoral artery, provides for an entry guide for other medical devices including the vascular closure device 12. Therefore, once the guide wire 15 is positioned in the vessel of the patient, catheters, or introducers, of gradually increasing diameters are advanced over the guidewire and through the puncture into the artery to further open the puncture site. Then, an introducer/procedure access sheath set (i.e. an introducer inside an access tube or sheath) is moved along the guide wire 15 such that a distal end of the sheath moves into the vessel through the puncture site. And once positioned, the introducer can be removed such that the sheath provides for sizable access to the vessel interior from outside the body.

After the relevant procedure is completed, the puncture site in the artery created by the bore needle during percutaneous access of the artery may be closed. The vascular closure system 10 as describe above and illustrated may be used to seal the puncture site. FIGS. 12A-12H show schematic views of the vascular closure system 10 during the process of closing a puncture site 200 in a vessel (e.g. artery) wall 204.

Figure 12A:
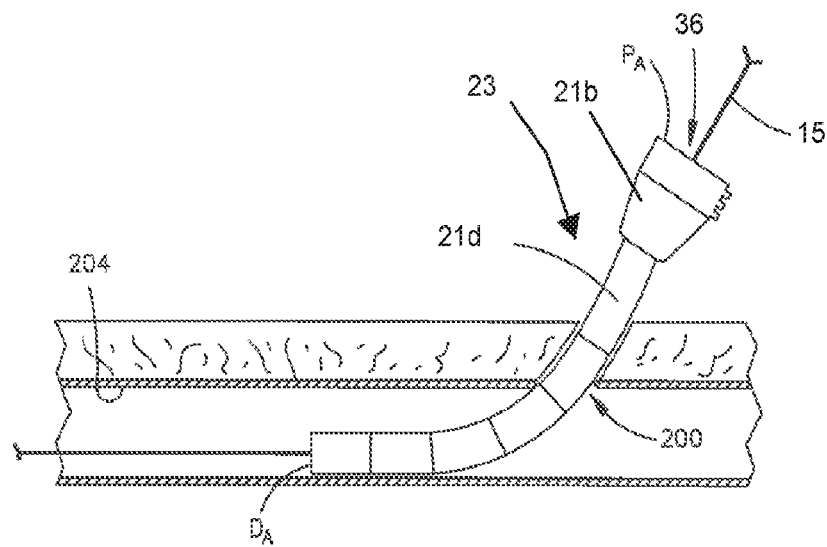

Now in reference to FIG. 12A, to deliver the vascular closure device 12 to the puncture site 200 so that the sealing element 18 can seal the puncture site 200, the introducer/procedure sheath set is replaced with a closure access sheath 23. For example, as shown in FIG. 12A, the procedure sheath is exchanged for the closure access sheath 23 by removing the procedure sheath from the patient, leaving the guide wire 15 in place, and subsequently moving the closure access sheath 23 along the guide wire 15 or otherwise positioning the access sheath 23, such that a portion of the access sheath 23 is disposed within the vessel through the puncture site 200. The access sheath 23, e.g. the sheath hub 21b, is configured to couple to the deployment assembly 14 when the deployment assembly 14 is inserted into the access channel 36 along the insertion direction I.

Figure 12B:
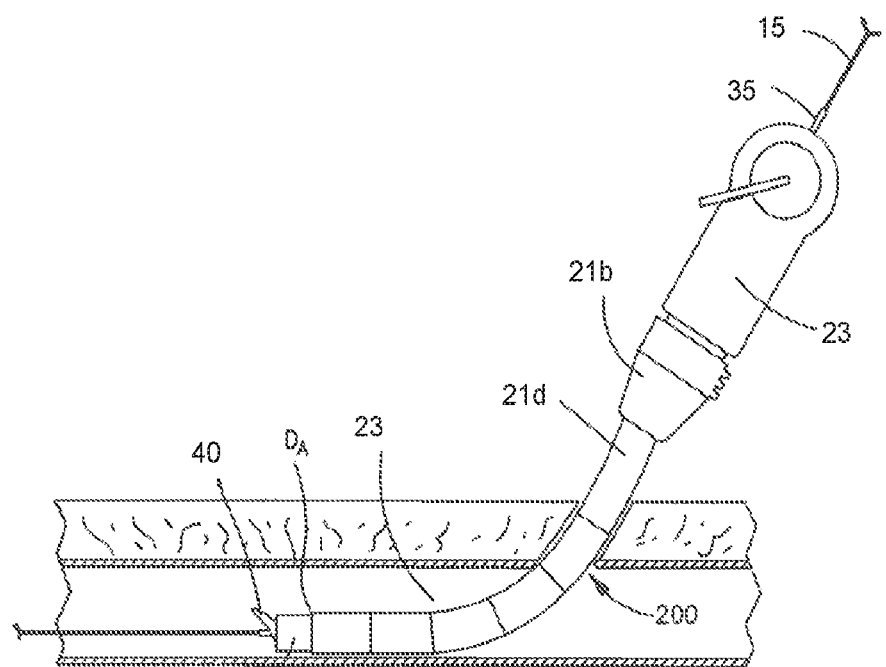

As shown in FIG. 12B, the vascular closure device 12 can be positioned by translating the vascular closure device 12 into the access channel 36 along the insertion direction I such that the toggle 40 protrudes from the distal end $D_A$ of the access sheath 23 and into the vessel. Once fully inserted, the deployment assembly 14 can couple to the sheath hub 21b. As shown in FIG. 12B, a proximal end the toggle 40 is trapped within the release component 22 between the release component 22 and the delivery component 26 while the vascular closure device 12 is being moved into the vessel through the puncture site 200 of the vessel. While the proximal end of the toggle 40 is trapped, the toggle 40 is oriented in a pre-sealing position whereby at least the proximal end of the toggle 40 is prevented from dragging against the vessel wall during positioning of the toggle 40 within the vessel.

Once the vascular closure device 12 is properly positioned within the access sheath 23, the toggle 40, and in particular, the entire access sheath 23 and vascular closure device 12 combination can be moved proximally such that the toggle 40 is adjacent the puncture site 200. While the toggle 40 is being positioned adjacent the puncture site 200 the toggle 40 is in the pre-sealing position as shown in FIG. 12C. And once the toggle 40 is in position, the actuator 38 is actuated to thereby release the toggle 40 from the release tube and subsequently apply a tension to the suture 44 so as to pull the toggle 40 against the distal end of the delivery component 26 as shown in FIG. 12D. At this point the toggle 40 will be oriented in the sealing position as shown in FIG. 12D and described previously.

With the toggle 40 in the sealing position as shown in FIG. 12D, the deployment assembly 14 along with the access sheath 23 can together be pulled proximally such that the toggle 40 abuts the vessel wall 204 as shown in FIG. 12E. As shown in FIG. 12F, further pulling of the deployment assembly 14 and sheath 23 will cause the sealing device 18, including the toggle 40, plug 88, a locking member 42, and suture 44 to be withdrawn from the delivery component 26. By pulling on the suture 44 in a direction away from the vessel (i.e. in a direction opposite the insertion direction I) the suture 44 is tensioned and the toggle 40 is moved fully into position against an inner surface of the vessel wall at the puncture site 200. The tension in the suture 44 also pulls and/or folds the plug 88 proximate the puncture site 200. Thus action causes the plug 88 to substantially fill the puncture site 200 as shown in FIG. 12F. After the plug 88 is in contact with blood or other fluids within the puncture site 200, the plug 88 will expand and fill the remainder of the puncture site 200. When tension reaches a threshold level, the locking assembly will release the tamper 110 so that it can be advanced out of the deployment assembly 14.

Figure 12G:
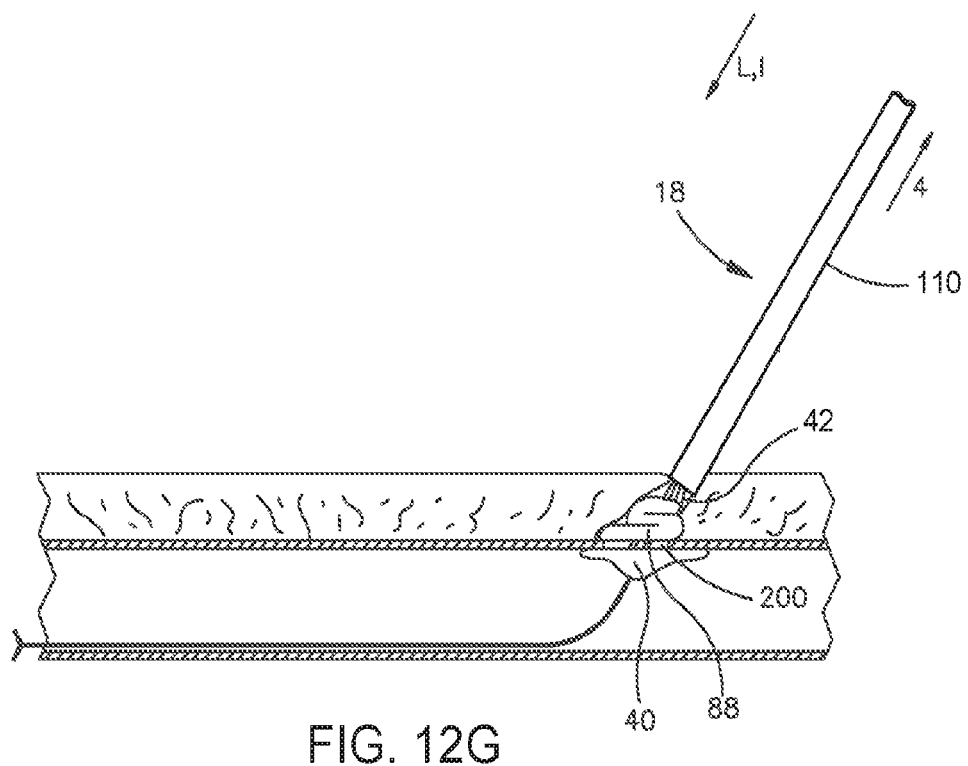
Figure 12H:
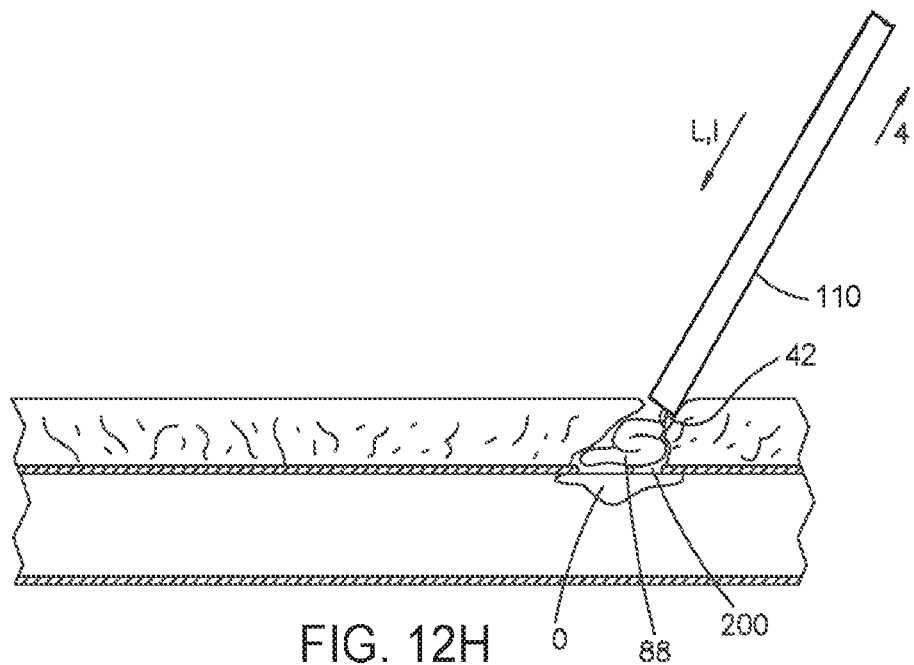

As shown in FIG. 12G, after the user has pulled the suture 44 to cause tension in the suture 44 and to cause the plug 88 to enter the puncture site 200, the user advances the tamper 110 along the guide wire 15 and the suture 44. As shown in FIG. 12H, the tamper 110 contacts the locking member 42 and advances the locking member 42 along the suture 44 until the locking member 42 contacts the plug 88 and presses the plug 88 against an outer surface of the vessel. As the plug 88 is compressed by the tamper 110 the plug 88 folds over the top of and inside the puncture site 200. It should be appreciated, however, that in some embodiments, the delivery component 26 is pulled such that the plug 88 is removed from the delivery component 26 within the release component 22 and the tamper 110 is employed within the release component 22. In such an embodiment, the release component 22 helps control the plug 88 as it is being tamped against the puncture site.

Figure 12I:
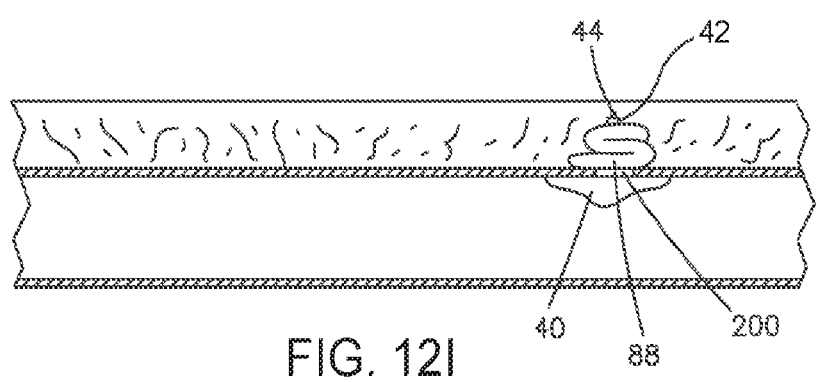

As shown in FIG. 12H, the locking member 42, together with the plug 88 and the toggle 40 seals the puncture site 200. As shown in FIG. 12H, tension is maintained on the suture 44 throughout the deployment of the plug 88 from the delivery component 26. After the puncture site 200 is sealed, the guide wire 15 can be removed as shown in FIG. 12I. As the guide wire 15 is removed, the suture 44 remains in tension and the user can re-compress the plug 88 with the tamper 110 as desired to confirm a proper seal of the puncture site 200. Once properly sealed, the suture 44 can be cut so that the remaining suture 44, tamper 110, and other components of the sealing device 18 can be removed from the puncture site 200, as shown in FIG. 12I. Remaining portions of the sealing device 18, including the toggle 40, plug 88, portion of suture 44, and locking member 42 (depending on material used) will resorb into the body of the patient over time.

While the foregoing description and drawings represent the preferred embodiment of the present invention, it will be understood that various additions, modifications, combinations and/or substitutions may be made therein without departing from the spirit and scope of the present disclosure as defined in the accompanying claims. In particular, it will be clear to those skilled in the art that the present disclosure may be embodied in other specific forms, structures, arrangements, proportions, and with other elements, materials, and components, without departing from the spirit or essential characteristics thereof. One skilled in the art will appreciate that the present disclosure may be used with many modifications of structure, arrangement, proportions, materials, and components, which are particularly adapted to specific environments and operative requirements without departing from the principles of the present disclosure. In addition, features described herein may be used singularly or in combination with other features. For example, features described in connection with one component may be used and/or interchanged with features described in another component. The presently disclosed embodiment is therefore to be considered in all respects as illustrative and not restrictive, the scope of the present disclosure being indicated by the appended claims, and not limited to the foregoing description.

It will be appreciated by those skilled in the art that various modifications and alterations of the present disclosure can be made without departing from the broad scope of the appended claims. Some of these have been discussed above and others will be apparent to those skilled in the art.

What is claimed:

1. A vascular closure device, comprising:
a deployment assembly that is elongate along a longitudinal direction and that has a distal end and a proximal end spaced from the distal end in a proximal direction that is aligned with the longitudinal direction;
a sealing unit carried by the deployment assembly, the sealing unit including a suture coupled to the deployment assembly;
a tamper carried by the deployment assembly and disposed along the suture with respect to the sealing unit in the proximal direction, the tamper including a lumen that receives the suture such that the tamper is slidable along the suture; and
a locking assembly coupled to the tamper so as to selectively inhibit advancement of the tamper along the suture in the distal direction toward the sealing unit, the locking assembly being adapted to transition from A) a locked configuration where the tamper is inhibited from sliding along the suture, into B) an unlocked configuration where the tamper is slidable along the suture in the distal direction and into contact with the sealing unit,
wherein the locking assembly includes at least one tab, the at least one tab including a respective opening that is sized to receive the tamper therethrough, wherein the at least one tab is moveable from a first position, where the tamper is inhibited from the sliding along the suture by the at least one tab such that the locking assembly is in the locked configuration, to a second position, where the tamper is slidable with respect to the at least one tab and along the suture such that the locking assembly is in the unlocked configuration.

2. The vascular closure device of claim 1, further comprising a tension element coupled to the suture and the locking assembly,
wherein the locking assembly transitions from the locked configuration into the unlocked configuration when tension applied to the suture exceeds a threshold level of tension,
wherein the tension element is responsive to the threshold level of tension applied to the suture so as to cause the locking assembly to transition from the locked configuration into the unlocked configuration.

3. The vascular closure device of claim 2, wherein the at least one tab is a first tab and a second tab, wherein at least one of the first tab and the second tab are configured to be biased toward each other of the first tab and the second tab when the tension applied to the suture exceeds the threshold level of tension such that the tamper is slidable through first and second openings.

4. The vascular closure device of claim 2, wherein the sealing unit includes a toggle attached to the suture and disposed at the distal end of the deployment assembly, a plug disposed along the suture with respect to the toggle in the proximal direction, and a locking member disposed along the suture with respect to the plug in the proximal direction.

5. The vascular closure device of claim 4, wherein the deployment assembly includes a release component and a delivery component, wherein the delivery component contains the locking member, the plug, and at least a portion of the tamper, and at least a portion of the toggle is captured between the release component and the delivery component.

6. The vascular closure device of claim 5, wherein the locking assembly is configured to transition into the unlocked configuration when A) the toggle is released from the between the release component and the delivery component, and B) the delivery component is advanced along the suture in the proximal direction so that the tension exceeds the threshold level of tension.

7. A vascular closure device, comprising:
a deployment assembly that is elongate along a longitudinal direction and that has a distal end and a proximal end spaced from the distal end in a proximal direction that is aligned with the longitudinal direction;
a sealing unit carried by the deployment assembly, the sealing unit including a suture coupled to the deployment assembly;

a tamper carried by the deployment assembly and disposed along the suture with respect to the sealing unit in the proximal direction, the tamper including a lumen that receives the suture such that the tamper is slidable along the suture, wherein the tamper includes a rear end and a forward end that is opposite the rear end, wherein the rear end of the tamper extends out the proximal end of the deployment assembly in the proximal direction, such that that the proximal end can be depressed so as to advance the tamper along the suture in the distal direction; and a locking assembly coupled to the tamper so as to selectively inhibit advancement of the tamper along the suture in the distal direction toward the sealing unit, the locking assembly being adapted to transition from A) a locked configuration where the tamper is inhibited from sliding along the suture, into B) an unlocked configuration where the tamper is slidable along the suture in the distal direction and into contact with the sealing unit.

8. The vascular closure device of claim 7, further comprising a tension element coupled to the suture and the locking assembly,
wherein the locking assembly transitions from the locked configuration into the unlocked configuration when tension applied to the suture exceeds a threshold level of tension,
wherein the tension element is responsive to the threshold level of tension applied to the suture so as to cause the locking assembly to transition from the locked configuration into the unlocked configuration.

9. A vascular closure device, comprising:
a deployment assembly that is elongate along a longitudinal direction and that has a distal end and a proximal end spaced from the distal end in a proximal direction that is aligned with the longitudinal direction;
a sealing unit carried by the deployment assembly, the sealing unit including a suture coupled to the deployment assembly;
a tamper carried by the deployment assembly and disposed along the suture with respect to the sealing unit in the proximal direction, the tamper including a lumen that receives the suture such that the tamper is slidable along the suture, and a notch; and
a locking assembly coupled to the tamper so as to selectively inhibit advancement of the tamper along the suture in the distal direction toward the sealing unit, the locking assembly being adapted to transition from A) a locked configuration where the tamper is inhibited from sliding along the suture, into B) an unlocked configuration where the tamper is slidable along the suture in the distal direction and into contact with the sealing unit, the locking assembly having a lever including an engagement end, wherein when the locking assembly is in the locked configuration the engagement end is disposed in the notch in the tamper such that the tamper is inhibited from sliding along the suture; and
a tension element coupled to the suture and the locking assembly, the tensioning element including an opening through which the lever extends, wherein when tension applied to the suture exceeds a threshold level of tension, the tension element is advanced in a direction to remove the engagement end from the notch such that the tamper is slidable along the suture, thereby causing the locking assembly to transition from the locked configuration into the unlocked configuration.

10. The vascular closure device of claim 9, wherein the locking assembly transitions from the locked configuration into the unlocked configuration when tension applied to the suture exceeds the threshold level of tension,
wherein the tension element is responsive to the threshold level of tension applied to the suture so as to cause the locking assembly to transition from the locked configuration into the unlocked configuration.

11. A vascular closure device, comprising:
a deployment assembly that is elongate along a longitudinal direction and that has a distal end and a proximal end spaced from the distal end in a proximal direction that is aligned with the longitudinal direction;
a sealing unit carried by the deployment assembly, the sealing unit including a suture coupled to the deployment assembly;
a tamper carried by the deployment assembly and disposed along the suture with respect to the sealing unit in the proximal direction, the tamper including a lumen that receives the suture such that the tamper is slidable along the suture, and a notch;
a tension element coupled to the suture; and
a locking assembly coupled to the tension element and the tamper so as to selectively inhibit advancement of the tamper along the suture in the distal direction toward the sealing unit, the locking assembly being adapted to transition from A) a locked configuration where the tamper is inhibited from sliding along the suture, into B) an unlocked configuration where the tamper is slidable along the suture in the distal direction and into contact with the sealing unit,
wherein the locking assembly includes a torsion member having at least one leg, wherein when the locking assembly is in the locked configuration, the at least one leg 1) abuts the tensioning element and 2) is engaged with the notch of the tamper such that the tamper is inhibited from sliding along the suture.

12. The vascular closure device of claim 11, further comprising a tension element coupled to the suture and the locking assembly,
wherein the locking assembly transitions from the locked configuration into the unlocked configuration when tension applied to the suture exceeds a threshold level of tension,
wherein the tension element is responsive to the threshold level of tension applied to the suture so as to cause the locking assembly to transition from the locked configuration into the unlocked configuration.

13. The vascular closure device of claim 12, wherein when tension is applied to the suture that exceeds the threshold level of tension, the tension element moves in a direction so as to permit the torsion member to rotate the at least one leg out of engagement with the notch.

14. A vascular closure device, comprising:
a deployment assembly that is elongate along a longitudinal direction and that has a distal end and a proximal end spaced from the distal end in a proximal direction that is aligned with the longitudinal direction;
a sealing unit carried by the deployment assembly, the sealing unit including a suture coupled to the deployment assembly;
a tamper carried by the deployment assembly and disposed along the suture with respect to the sealing unit in the proximal direction, the tamper including a lumen that receives the suture such that the tamper is slidable along the suture, and a notch; and a locking assembly coupled to the tamper so as to selectively inhibit advancement of the tamper along the suture in the distal direction toward the sealing unit, the locking assembly being adapted to transition from A) a locked configuration where the tamper is inhibited from sliding along the suture, into B) an unlocked configuration where the tamper is slidable along the suture in the distal direction and into contact with the sealing unit, wherein the locking assembly includes an engagement member through which the suture passes, and a biasing member, wherein when the locking assembly is in the locked configuration the biasing member urges the engagement member into the notch in the tamper such that the tamper is inhibited from sliding along the suture.

15. The vascular closure device of claim 14, further comprising a tension element coupled to the suture and the locking assembly, wherein the locking assembly transitions from the locked configuration into the unlocked configuration when tension applied to the suture exceeds a threshold level of tension, wherein the tension element is responsive to the threshold level of tension applied to the suture so as to cause the locking assembly to transition from the locked configuration into the unlocked configuration.

16. The vascular closure device of claim 15, wherein when the tension applied to the suture exceeds the threshold level of tension, the suture biases the engagement member out of the notch such that the tamper is slidable along the suture.

17. A vascular closure device, comprising:
a deployment assembly that is elongate along a longitudinal direction and that has a distal end and a proximal end spaced from the distal end in a proximal direction that is aligned with the longitudinal direction;
a sealing unit carried by the deployment assembly, the sealing unit including a suture coupled to the deployment assembly;
a tension element coupled to the suture;
a tamper carried by the deployment assembly and disposed along the suture with respect to the sealing unit in the proximal direction, the tamper including 1) a lumen that receives the suture such that the tamper is slidable along the suture, and 2) a notch; and
a locking assembly coupled to the tension element and the tamper so as to selectively inhibit advancement of the tamper along the suture in the distal direction toward the sealing unit, the locking assembly being adapted to transition from A) a locked configuration where the tamper is inhibited from sliding along the suture, into B) an unlocked configuration where the tamper is slidable along the suture in the distal direction and into contact with the sealing unit, wherein the locking assembly includes a tab having a recess, and a biasing member coupled to the tab, wherein the tension element includes a projection that is moveable along with tension element, wherein when the locking assembly is in the locked configuration, the projection is in the recess so as to maintain the tab in engagement with the notch of the tamper such that the tamper is inhibited from sliding along the suture.

18. The vascular closure device of claim 17, wherein the locking assembly transitions from the locked configuration into the unlocked configuration when tension applied to the suture exceeds a threshold level of tension, wherein the tension element is responsive to the threshold level of tension applied to the suture so as to cause the locking assembly to transition from the locked configuration into the unlocked configuration.

19. The vascular closure device of claim 18, wherein when tension is applied to the suture that exceeds the threshold level of tension, the tension element is advanced in a direction to remove the projection from the recess, thereby permitting the biasing member to retract the tab out of the notch such that the tamper is slidable along the suture.

20. The vascular closure device of claim 1, wherein the at least one tab is at least one plate.

* * * * *